(12) United States Patent
Oura

(10) Patent No.: US 7,146,743 B2
(45) Date of Patent: Dec. 12, 2006

(54) LENGTH MEASURING INSTRUMENT

(75) Inventor: Yasushi Oura, Kita-ku (JP)

(73) Assignee: Oura Kousoku Co., Ltd., Tokyo (JP)

(*) Notice: Subject to any disclaimer, the term of this patent is extended or adjusted under 35 U.S.C. 154(b) by 32 days.

(21) Appl. No.: 10/534,273

(22) PCT Filed: Nov. 14, 2003

(86) PCT No.: PCT/JP03/14491

§ 371 (c)(1),
(2), (4) Date: May 9, 2005

(87) PCT Pub. No.: WO2004/046639

PCT Pub. Date: Jun. 3, 2004

(65) Prior Publication Data
US 2006/0021244 A1 Feb. 2, 2006

(30) Foreign Application Priority Data

Nov. 19, 2002 (JP) ............................. 2002-334879
Aug. 27, 2003 (JP) ............................. 2003-303482

(51) Int. Cl.
G01B 3/10 (2006.01)
G01D 5/347 (2006.01)

(52) U.S. Cl. ..................... 33/756; 33/555.4; 33/707
(58) Field of Classification Search .............. 33/750, 33/754, 755, 756, 761, 762, 763, 767, 768, 33/770, 772, 773, 774, 776, 780, 511, 512, 33/555.4, 707

See application file for complete search history.

(56) References Cited

U.S. PATENT DOCUMENTS

| 809,139 | A | * | 1/1906 | Saxton | 33/761 |
| 1,424,085 | A | * | 7/1922 | Crogan | 33/768 |
| 2,410,713 | A | * | 11/1946 | Carlson | 242/396.5 |
| 2,854,753 | A | * | 10/1958 | Caparros | 33/762 |
| 4,092,780 | A | * | 6/1978 | Trethewey et al. | 33/762 |
| 4,587,738 | A | * | 5/1986 | Kang | 33/762 |

(Continued)

FOREIGN PATENT DOCUMENTS

JP 57-64604 A 4/1982

(Continued)

Primary Examiner—G. Bradley Bennett
Assistant Examiner—Amy R. Cohen
(74) Attorney, Agent, or Firm—Connolly Bove Lodge & Hutz LLP

(57) ABSTRACT

A length measuring instrument capable of measuring, displaying and recording the length around a part being measured by applying a measuring belt tightly to that part and operating the instrument by single hand. A rotary shaft disposed in a housing is provided with a spiral spring, the measuring belt, and an optical modulating section having a part for regulating the quantity of transmitted light. The belt is drawn out and applied tightly to the circumference of the part being measured. The rotary shaft is rotated forward when the belt is drawn out and rotated reversely by the recovering force of the spring to pull in the belt automatically thus, stretching and tensioning the belt. The light is converted into an optical modulation signal L depending on the rotation of optical modulating section and that signal is converted temporarily into a photoelectric conversion signal before being converted into an electric signal. The pulse generation pattern is judged at the forward/reverse rotation judging section of 2a CPU, addition and subtraction counting is performed at the pulse counting section in response to the judgment results, and the value of a length corresponding to the final count is read out from a storage device and displayed at a display section.

18 Claims, 13 Drawing Sheets

U.S. PATENT DOCUMENTS

| | | | |
|---|---|---|---|
| 4,642,899 A * | 2/1987 | Fass et al. | 33/760 |
| 4,920,659 A * | 5/1990 | Becher | 33/555.4 |
| 5,027,526 A * | 7/1991 | Crane | 33/763 |
| 5,060,394 A * | 10/1991 | Lincoln et al. | 33/763 |
| 5,367,785 A * | 11/1994 | Benarroch | 33/767 |
| 5,406,715 A * | 4/1995 | Koizumi et al. | 33/706 |
| 5,743,021 A * | 4/1998 | Corcoran | 33/762 |
| 6,817,110 B1 * | 11/2004 | Bohnengel | 33/555.4 |
| 6,898,866 B1 * | 5/2005 | Weeks | 33/762 |

FOREIGN PATENT DOCUMENTS

| | | |
|---|---|---|
| JP | 60-179903 A | 11/1985 |
| JP | 07-115881 A | 5/1995 |
| JP | 08-310699 A | 11/1996 |
| JP | 09-166432 A | 6/1997 |
| JP | 11-264702 A | 9/1999 |

* cited by examiner

LENGTH MEASURING INSTRUMENT

TECHNICAL FIELD

The present invention relates to a length measuring instrument suitable for measuring the circumferential length of the part being measured by substantially tightly applying a measuring belt to the part.

BACKGROUND ART

A winding tape instrument made of a cloth and having a configuration with automatic rewinding using a spiral spring has been known (Japanese Patent Application Laid-open No. 11-264702) as a tool for measuring the thickness of parts of human or animal body. When a waist is measured for higher accuracy by using the winding tape instrument, the measurements are conduced in a state in which the measuring belt of the winding tape instrument is stretched tightly, without a slack, around the waist, that is, in a state in which the measuring belt is tensioned. When the size of the body part is thus measured with the winding tape instrument, it is necessary to stretch the measuring belt and apply tension thereto, that is, to pull out all the slack.

Further, a method for measuring the length of a fishing line by using a magnet and a Hall IC has also been suggested. However, because a pair of Hall IC and magnets provided in separate places was used as means for judging the rotation direction of the spool (forward or reverse rotation direction) and measuring means, the configuration was complex and the size was large (Japanese Patent Application Laid-open No. 7-115881).

Moreover, a method for determining the draw-out length, that is, the travel distance of a film wound on a rotary shaft by using a number of pulse signals from an encoder provided on the rotary shaft has also been suggested, but film rewinding was not assumed in any way (Japanese Patent Application Laid-open No. 8-310699).

DISCLOSURE OF THE INVENTION

If a measuring belt wound around a part being measured is strongly tensioned, the belt is pressed into the part. Therefore, accurate measurements are impossible and in addition a pain is created in the part which is being measured. On the other hand, if the measurements are conducted by loosely winding the measuring belt around the part being measured, the measured value is larger than the actual value due to the slack of the measuring belt and accurate measurements cannot be conducted.

Further, even when a person himself measures his own part by using the conventional winding tape instrument, for example, measures the thickness of one wrist, the measurements are difficult to conduct with the other hand and the measurement results are inaccurate.

With the foregoing in view, the inventors have conducted comprehensive research and repeated tests aimed at the resolution of the above-described problems. The results obtained demonstrated the following.

(1) A belt can be substantially tightly applied to the part being measured by rewinding the measuring belt that was drawn out and tightening the melt, that is, pulling a slack out of the belt itself.

(2) The draw-out quantity of the measuring belt wound around a rotary shaft corresponds to the rotation quantity of the rotary shaft. Therefore, if an optical modulating section is provided on the rotary shaft, optical conversion signals with different optical modulation state are acquired, and those optical modulation signals are converted into electric pulses, then the forward or reverse rotation of the rotary shaft can be judged by the pattern of pulse trains of the electric pulses. Furthermore, the draw-out length can be determined from the final count value obtained by addition or subtraction counting the number of electric pulses according to the forward or reverse rotation.

(3) If the measuring belt is drawn out in advance to form a ring and the measurements are conducted by passing the part being measured into this ring, then the measurements can be easily conducted with one hand.

It is a first object of the present invention to provide a length measuring instrument with a configuration enabling more accurate measurements by substantially tightly applying the measuring belt to the part being measured.

It is a second object of the present invention to provide a length measuring instrument with a configuration allowing the length of the part being measured to be measured by operations with one hand only.

It is a third object of the present invention to provide a length measuring instrument with a configuration such that the measurement value of the part being measured can be calculated automatically and accurately when either drawing out or rewinding of the measuring belt is conducted.

It is a fourth object of the present invention to provide a length measuring instrument with a small configuration which is easy to operate.

The measuring instrument for measuring the length of a part being measured by the draw-out length of a measuring belt in accordance with the present invention comprises a housing, a rotary shaft, a measuring belt, a rotary shaft drive unit, an optical modulating section, a measurement unit, and a latching section provided outside the housing.

The rotary shaft is rotatably held inside the housing.

The measuring belt is wound around the rotary shaft so that one end portion thereof is fixed to the rotary shaft. A latching tool is provided on the other end portion of the measuring belt. The rotary shaft is rotated in the forward direction when the other end portion side of the measuring belt is pulled and the measuring belt is drawn out to the outside of the housing.

The rotary shaft drive unit is provided inside the housing and designed to rewind the measuring belt, which has been drawn out, by rotating the rotary shaft in the reverse direction, that is, to draw the measuring belt in. The rotary shaft drive unit in combination with the rotary shaft constitutes the draw-in mechanism.

The optical modulating section is provided in communication with the rotary shaft and converts the light from a light source into optical modulation signals.

The measurement unit is provided inside the housing for converting the optical modulation signals into electric pulse signals, counting the number of the electric pulse signals, determining the draw-out length of the measuring belt from the counted number, and displaying the determined length as a measurement result.

The measurement unit comprises a light source, a photoelectric conversion unit, a pulse formation circuit, and a length determination unit. The photoelectric conversion unit converts the light received from the light source via the optical modulating section into photoelectric conversion signals. The pulse formation circuit converts the photoelectric conversion signals into electric pulse signals. The length determination unit comprises a forward/reverse rotation judging section for judging whether the rotary shaft rotates into forward direction or reverse direction from the electric pulse signals, and a pulse counting section. When the forward/reverse rotation judging section decides that the rotation is in the forward direction, the pulse counting section addition counts the number of the electric pulse signals, and when the forward/reverse rotation judging section decides that the rotation is in the reverse direction, the pulse counting section subtraction counts the number of the electric pulse signals. The pulse counting section outputs the final count number obtained as a result of the addition counting and subtraction counting as the measurement result. The length determination unit is constituted as functional means for the CPU of a microcomputer (μC).

The latching section latches the latching tool of the measuring belt and cues the measuring belt. Furthermore, it also serves to latch the latching tool for in order to form a ring of the measuring belt during measurements.

The above-described optical modulating section, measurement unit, and latching section constitute a measurement mechanism for measuring the feed length of the measuring belt.

With the above-described configuration of the length measuring instrument in accordance with the present invention, the state in which revealing a foremost edge of the measuring belt has been conducted can be considered as a reference point in which the draw-out quantity, that is, the draw-out length of the belt is zero. The belt is drawn out starting from this state, the belt is tightly wound around the part being measured, and the latching tool is latched with the latching section. When the belt is thus drawn out, the rotary shaft is rotated in the forward direction and optical modulation signals are output from the optical modulating section.

The optical modulating section conducts conversion into optical modulation signals with the pulse formation circuit of the measurement unit. Each pulse of the electric pulse signals is supplied to the forward/reverse rotation judging section and pulse counting section. In the forward/reverse rotation judging section, a decision is made as to whether the rotary shaft rotates in the forward or reverse direction based on the modulation state of the pulse train of the electric pulse signals. When no slack is present in the belt, the rotary shaft is decided to rotate forward.

If the rotary shaft is judged to rotate forward, the number of pulses corresponding to the draw-out quantify of the belt is counted. This count is determined as the draw-out length of the measuring length and displayed.

When the belt is not tightly wound around the part being measured, or when a slack is present in part of the belt that was drawn out, the rotary shaft drive unit rewinds the belt by causing the rotary shaft to rotate in reverse automatically or by operation control and the belt assumes a strongly tensioned state without a loose portion. In this case the forward/reverse rotation judging section makes decides that the rotary shaft rotates in reverse. Therefore, the number of pulses generated during this reverse rotation is counted.

In accordance with the decision of the forward/reverse rotation judging section, the pulse counting section conducts the addition counting or subtraction counting from the addition count number, determines the final count number, and outputs it. The final count number is determined and displayed as the draw-out length, that is, the measurement result.

The length measuring instrument in accordance with the present invention preferably also comprises a guiding unit having the prescribed length and formed on the outer side surface of the housing. The guiding unit comprises a distal end section provided with the latching section. The measuring belt that has been drawn out from the housing is guided along the guiding unit till this distal end section is reached. As a result of this latching, the measuring belt is cued. This guiding unit is fixed to the side surface of the housing.

Alternatively, the length measuring instrument in accordance with the present invention is further provided with the guiding unit formed as a rod-like or bar-like body having the prescribed length and connected to the outer side of the housing. One end section of the rod-like body is rotatably connected to the housing. The other end section of the rod-like body serves as the distal end section where the latching section is provided. The measuring belt that has been drawn out from the housing is guided with the guiding unit till this distal end section is reached, and the latching tool is latched with the latching section, thereby cueing the measuring belt. In this case, the configuration allows the guiding unit to rotate with respect to the housing.

Thus, with the configuration in which the guiding unit is provided as part of the measuring mechanism in the length measuring instrument, the distal end portion of the guiding unit can serve as a reference point of the draw-out length, and this reference point can be set into a position distant from the opening of the housing for drawing out the measuring belt. If the top surface of the distal end portion of the guiding unit is brought into contact with the part being measured during measurements, the belt is tightly tensioned, without slack, by the action of the above-described rotary shaft drive unit, the belt is brought into intimate contact with the part being measured, and the intermediate portion of the belt, from the distal end section of the guiding unit to the rotary shaft, is tightly tensioned without a slack.

The optical modulating section preferably comprises a rotary optical modulation plate provided, directly or indirectly, on the rotary shaft. Thus, instead of fixing this rotary optical modulation plate, directly or indirectly, on the rotary shaft, it may be linked to this rotary shaft and provided on another rotatable rotary shaft. When the rotary optical modulation plate is directly provided on the rotary shaft, the rotation speed of the rotary optical modulation plate is equal to the rotation speed of the rotary shaft. On the other hand, when the rotary optical modulation plate is provided on a rotary shaft that is different from the aforementioned rotary shaft, the rotation speed of the rotary optical modulation plate can be higher than the rotation speed of the rotary shaft.

The rotary optical modulation plate preferably comprises a transparent disk and a plurality of portions for regulating the quantity of transmitted light, those portions being arranged successively and adjacently on the surface of the transparent disk.

The portions for regulating the quantity of transmitted light may be in the form of light-shielding areas and light-transmitting areas of different width in the rotation direction of the rotary optical modulation plate. Alternatively, the portions for regulating the quantity of transmitted light are preferably light-transmitting areas with different light transmittances.

With such an optical modulating section, if the regulating portions with different light transmission quantity are arranged repeatedly, then electric pulse signals of different pulse train patterns can be obtained during forward and reverse rotation of the rotary shaft. Therefore, a judgment relating to forward or reverse rotation is facilitated.

Further, it is also preferred that a semiconductor light-emitting element may be used as the light source, a semiconductor light-receiving element be used as the photoelectric conversion unit, and the semiconductor light-emitting element and semiconductor light-receiving element be disposed opposite each other so as to sandwich the optical modulating section therebetween.

Further, it is also preferred that the rotary shaft drive unit may be a spiral spring or an electrically operated motor (also called "electric motor").

The above-described measurement unit preferably further comprises a storage device for recording the measurement information such as a display mode and the measurement results in a readable form, a display section for displaying the measurement information, an input unit for selectively inputting a variety of commands instructing to select the displayed measurement information, determine the recording of measurement result, and clear the measurement information displayed in the display section, and a display control unit for controlling the display in the display section according to the command from the input unit. Those display section and display control unit constitute a display mechanism.

With all the length measuring instruments described in the claims the following merits can be demonstrated.

(1) The measuring belt can be brought into intimate contact with the part being measured and measurements can be conducted in a state in which the measuring belt is tightly tensioned, without a slack. Therefore, the measurements can be conducted more accurately than with the conventional instruments of this type.

In particular, with the configuration comprising the guiding unit, the measurements can be conducted by pushing the aforementioned distal end section against the part being measured after the measuring belt has been wound around the part being measured and the belt portion was tensioned. In this case, the belt portion guided by the guiding unit is held without a slack. Therefore, the entire portion of the measuring belt that has been unwound from the rotary shaft can be tightened and, therefore, accurate measurements can be conducted.

(2) When the part of one hand is measured, the latching tool at the distal end section of the measuring belt is engaged in advance with the latching section provided on the outer side of the housing and a ring is formed. The part being measured is passed through the ring and then the measurement operation is conducted. Therefore, the measuring instrument can be readily operated with the other hand.

(3) The draw-out length of the belt that was drawn out can be automatically measured because the configuration is employed in which the optical modulation signals from an optical modulating section provided in correspondence with the rotary shaft are converted into electric pulse signals in the measurement unit and the number of pulses is counted.

(4) Not only in the case where the measuring belt was drawn out and tightened without a slack, but also when there was a slack in the drawn-out belt, because the measuring belt is rewound and the belt is tightened, the final draw-out length of the belt can be measured more accurately than with the conventional instruments. In particular, when a spiral coil is used as the rotary shaft drive unit, the rewinding of the measuring belt can be conducted automatically even though no special rewinding means is provided.

(5) Further, in particular, when the optical modulating section is composed of a rotary optical modulation plate and portions for regulating the quantity of transmitted light provided on the rotary optical modulation plate, the light falling on the portions for regulating the quantity of transmitted light is converted by those portions for regulating the quantity of transmitted light into optical modulation signals with different duration interval or light intensity. Forward or reverse rotation is judged by converting those optical modulation signals into electric pulse signals and detecting pulse train patterns of the pulses of the electric pulse signals. Therefore, forward or reverse rotation can be judged more accurately. As a result, the electric pulse signals can be addition or subtraction counted with higher accuracy. The light intensity of the optical modulation signals that passed through the regulating portions with different quantity of transmitted light may be same or different. If the duration interval of optical modulation signals is different, it is merely a design task to regulate the light intensity. Furthermore, when the light intensity of the optical modulation signals is different, the duration interval may be same or different.

(6) Because no large and complex structural components are used, the configuration can be small and simple to operate.

BEST MODE FOR CARRYING OUT THE INVENTION

Figure 1:
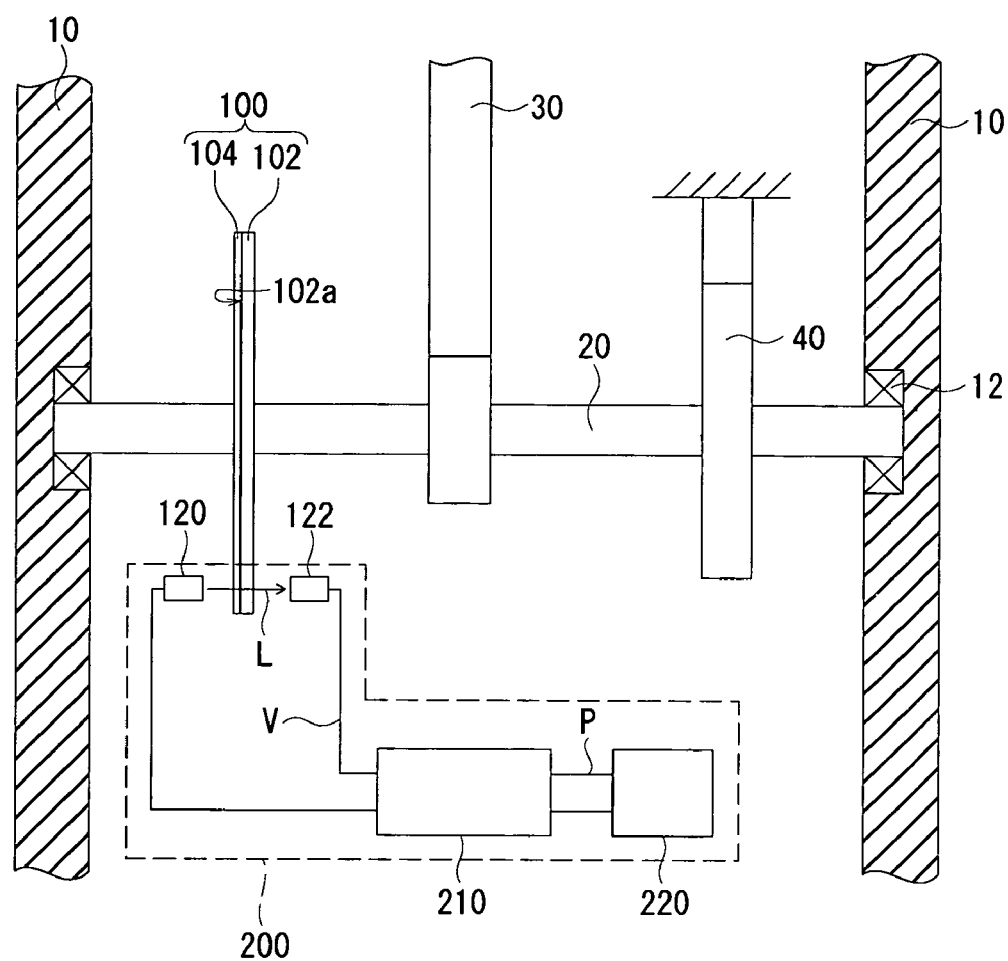
FIG. 1 is a view for illustrating schematically, with partial cross section, an example of the main configuration of a length measuring instrument in accordance with the present invention.

Embodiments of the length measuring instrument in accordance with the present invention will be described below with reference to the drawings. In the drawings, the shape, size and mutual arrangement of structural elements are shown schematically on such a level that the invention can be easily understood. The configuration examples shown in the figures merely illustrate the preferred examples, and accordingly, these inventions are not limited to the illustrated embodiments.

Figure 2:
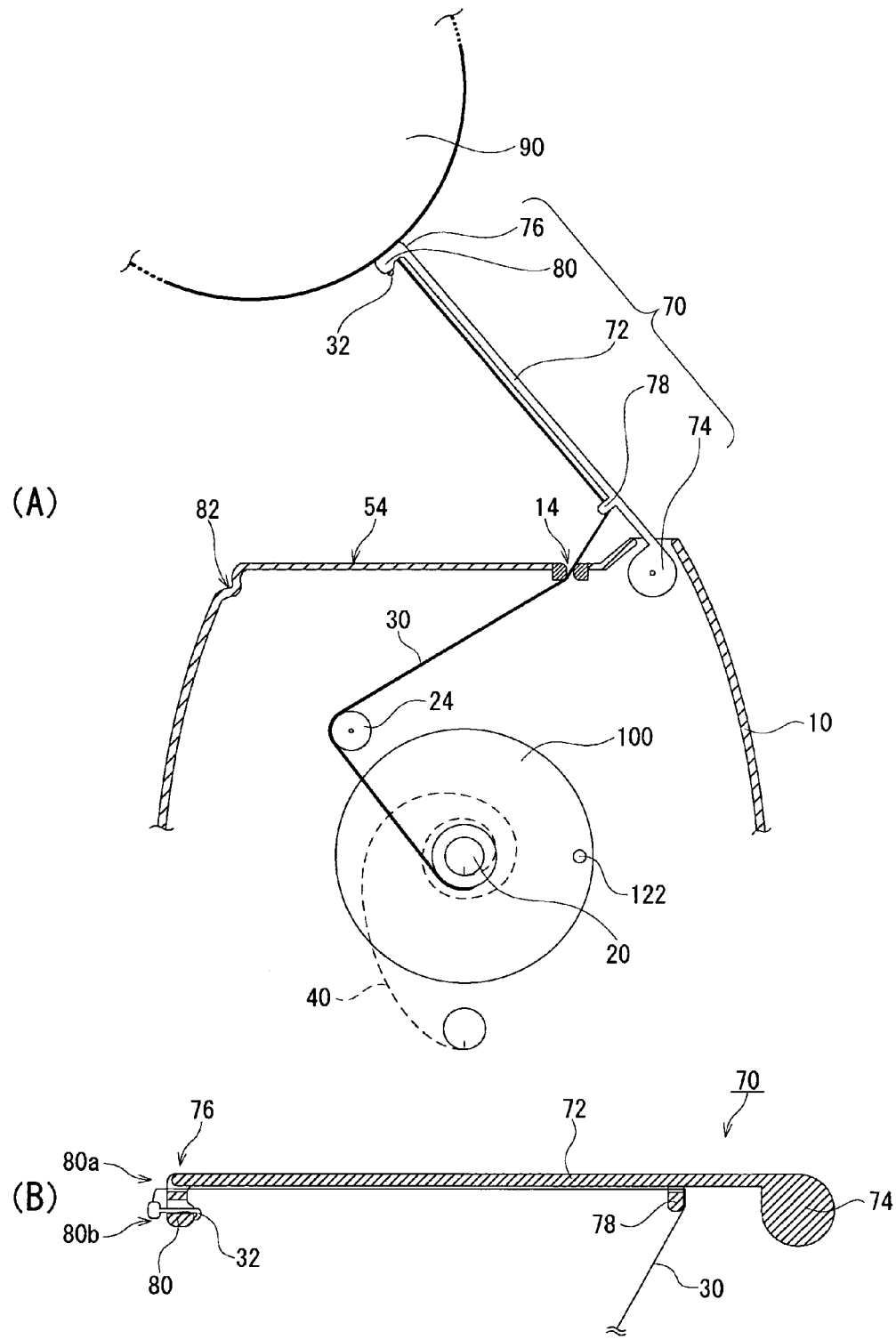
FIG. 2(A) is a schematic structural view, with a partial cross section, for providing explanation of an example of the rotary shaft drive unit and guiding unit constituting the length measuring instrument in accordance with the present invention.
FIG. 2(B) is a schematic cross-sectional view of the guiding unit.
Figure 3:
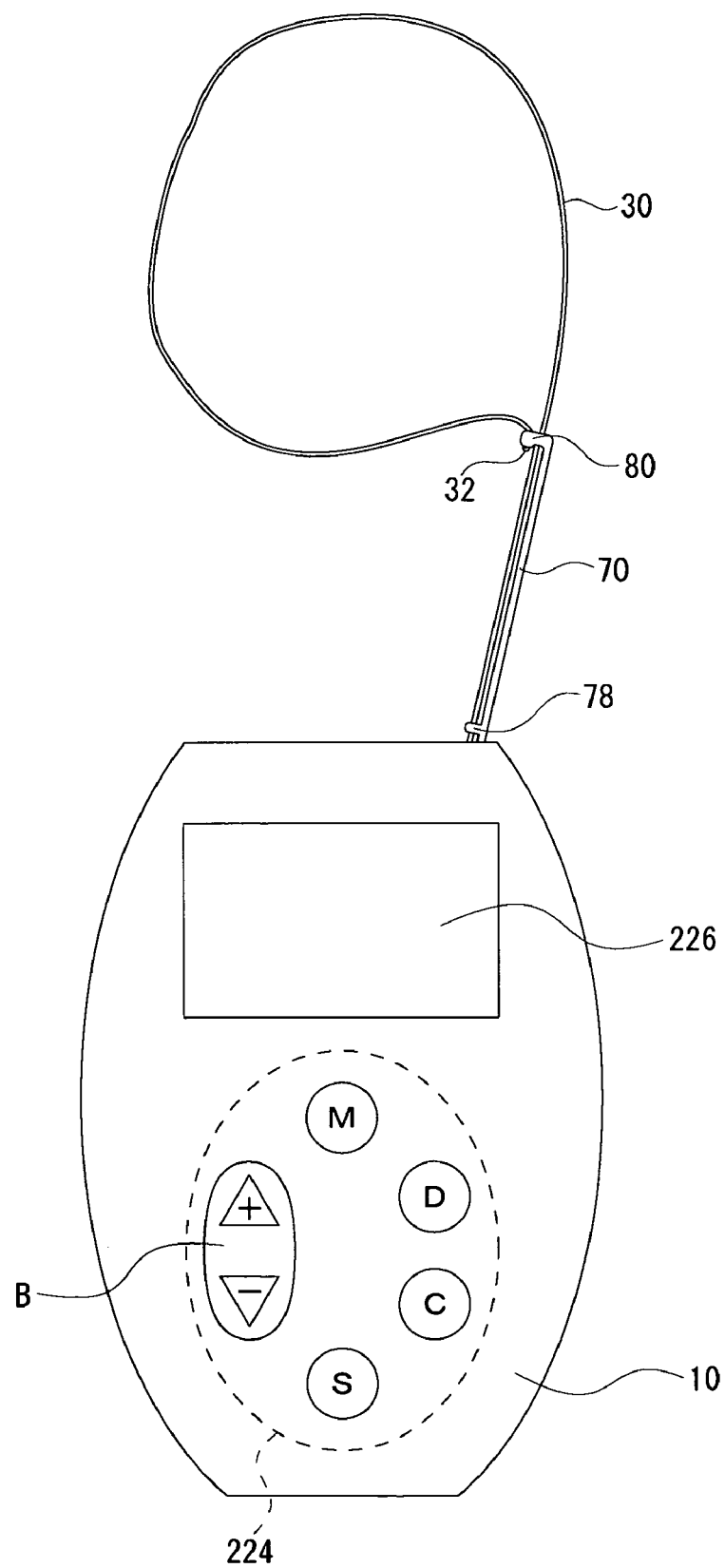
FIG. 3 is a schematic view illustrating a configuration example representing the external appearance of the length measuring instrument in accordance with the present invention.

FIG. 1 and FIG. 2(A) are schematic drawings illustrating the main components for explaining the basic configuration of the length measuring instrument in accordance with the present invention. FIG. 2(B) is a schematic longitudinal sectional view for explaining one configuration example of the guiding portion which is a structural element in accordance with the present invention. FIG. 3 is a plan view showing schematically an example of the image design of the external appearance of the length measuring instrument.

The length measuring instrument in accordance with the present invention comprises a housing 10 (it can be also referred to as a casing), a rotary shaft 20, a measuring belt 30, a rotary shaft drive unit 40, an optical modulating section 100, a measurement unit 200, and a latching section 50 (or 80) provided outside the housing.

The housing 10 is formed from any appropriate material, for example, a plastic, and the below-described display section 226 and input unit 224 having a variety of control buttons are provided on the housing plate on the front surface of the housing. Not only the shape and size of the housing, but also the number, size, and mutual arrangement of the display section and control buttons are merely the design issues.

The rotary shaft 20 is rotatably supported inside the housing 10 with appropriate support means such as a bearing 12. The measuring belt 30 is fixed by one end portion thereof to the rotary shaft 20 and wound around the rotary shaft 20 by an appropriate number of turns. In this case, the measuring belt may be from a cloth or a plastic. The measuring belt may be formed from a material that cannot be stretched or shrunk or a material that can stretch or shrink to a degree producing no effect on measurement results. It is preferred that the measuring belt be from a strong, lightweight and flexible material, but any suitable material may be selected according to the design thereof. Furthermore, when the length of the measuring belt is 1 m, 2 m or more, from the standpoint of the belt thickness after winding on the rotary shaft, it is preferred that the measuring belt may be formed from as thin a material as possible.

Further, if desired, the measuring belt may be provided on an appropriate rotary unit linked to the rotary shaft, and such a configuration may be employed, provided that the size and weight of the measuring instrument are decreased. In FIG. 2(A) a tension pulley 24 is shown, but this pulley 24 is not a mandatory component.

The below-described latching tool is provided at the other end of the measuring belt 30. The rotary shaft 20 is rotated by pulling the other end side of the measuring belt and drawing the measuring belt out of the housing.

The rotary shaft drive unit 40 is provided inside the housing 10 and employed to rotate the rotary shaft 20 in reverse and to rewind the measuring belt 30 that was drawn out. For this reason, the rotary shaft drive unit 40 may be also called a draw-in mechanism of the measuring belt. How to link the rotary unit 40 to the rotary shaft is merely a design feature. In the present configuration example, it is preferred that the drive unit be directly linked to the rotary shaft 20 to reduce the size of the measuring instrument. Spring means or a small electric motor can be used as the drive unit.

In the configuration example shown in FIG. 1 and FIG. 2(A), the rotary shaft drive unit 40 is preferably a spiral spring. If the measuring belt 30 is drawn out, the rotary shaft 20 rotates forward against the elastic force of the spiral spring 40. If the tension force causing the rotary shaft 20 to rotate forward against the aforementioned elastic force is released, the spiral spring 40 generates a recovering force that acts to restore the original state and automatically rotates the rotary shaft 20 in reverse. Therefore, the measuring belt 30 that was drawn out is automatically wound on the rotary shaft 20. For this reason, no special means is required to rotate the rotary shaft 20 in reverse. This configuration is thus preferred because it allows the size and weight of the measuring instrument to be decreased and the operations to be facilitated.

The measuring belt is tensioned by the tensile force corresponding to the drive force of the rotary shaft drive unit 40. This tensile force can be set to any value according to the design.

When an electric motor is used as the rotary shaft drive unit 40, a special switch or a power transmission mechanism composed, for example, of a set of gears and located between the rotary shaft and the electric motor shaft are required to control the operation of the electric motor. Therefore this configuration is somewhat inferior to that using a spiral spring from the standpoint of reducing the size of the instrument and facilitating the operation.

The optical modulating section 100 is mounted on the rotary shaft 20 inside the housing 10 and serves to convert the light from a light source 120 into an optical modulation signal L.

In this configuration example, the optical modulating section 100 is composed of a rotary optical modulation plate directly fixed to the rotary shaft 20. The rotary optical modulation plate 100 preferably has a configuration comprising a transparent disk 102 and a plurality of portions for regulating the quantity of transmitted light (denoted by a reference numeral 104), those portions being provided in a successively adjacent arrangement of the surface of the transparent disk 102.

The transparent disk 102 is formed, for example, from a plastic and any suitable transparent material, preferably, in the form of a film capable of withstanding the rotation drive. From the standpoint of utility, that is, miniaturization of the measuring instrument, it is preferred that the maximum diameter of the transparent disk may be about 5 cm, but this size is not limiting.

Figure 4:
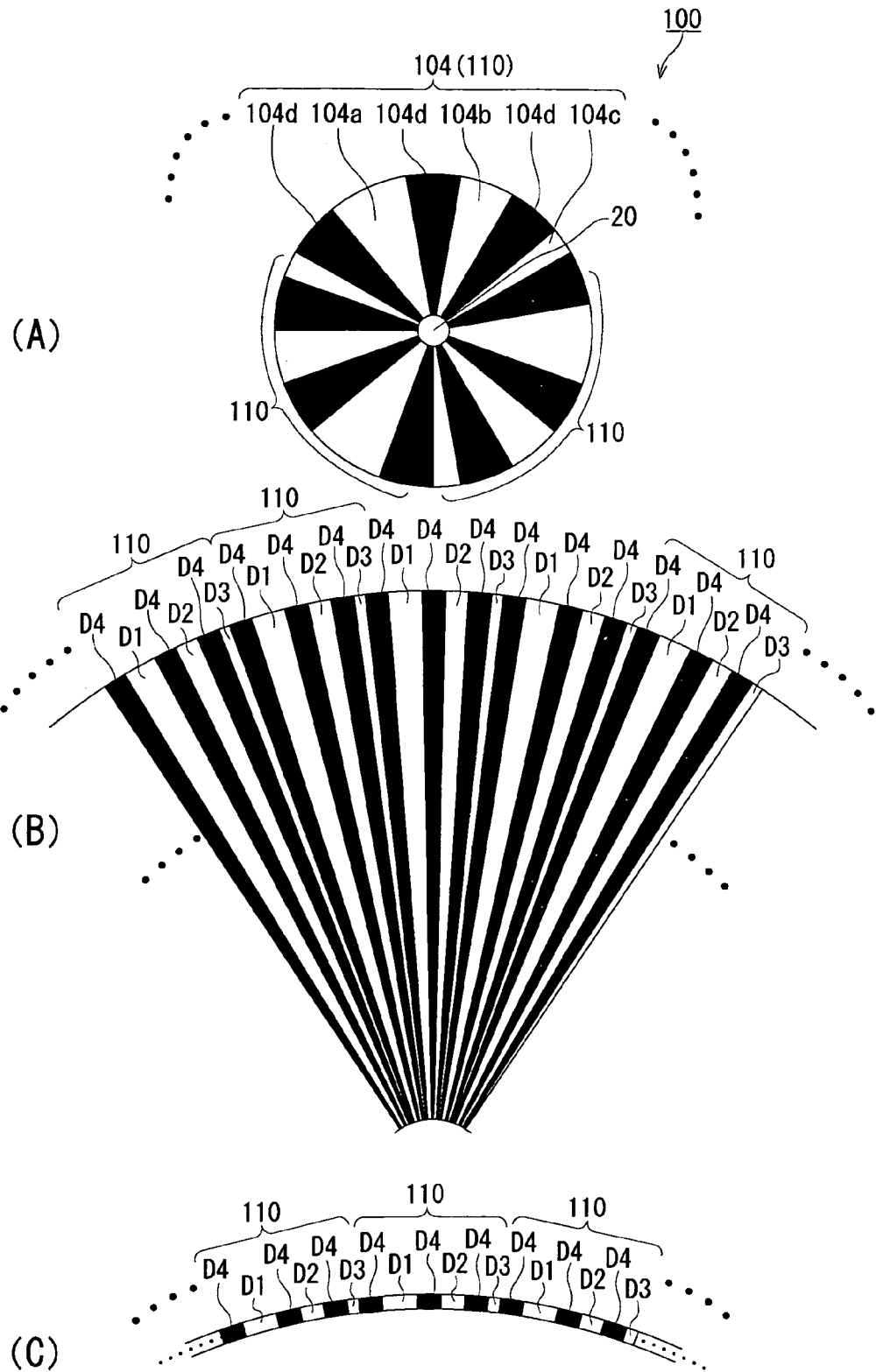
FIGS. 4(A), (B), and (C) are views for providing explanation of an example of the optical modulating section constituting the length measuring instrument in accordance with the present invention.

FIG. 4(A) is a plan view from the side of the portions for regulating the quantity of transmitted light, which is used to explain a basic configuration example of the rotary optical modulation plate 100. FIGS. 4(B) and (C) serve to explain the portions 104 for regulating the quantity of transmitted light. The portions 104 for regulating the quantity of transmitted light are provided on a main surface 102a on one side of the transparent disk 102. All the portions 104 for regulating the quantity of transmitted light or some of them are preferably formed as a film, for example, by vapor deposition, printing, photographic imprinting, or any other appropriate means. The formation method of the portions 104 for regulating the quantity of transmitted light does not represent the essence of the present invention and detailed explanation thereof is omitted. Other methods can be also used to form the section.

The portions 104 for regulating the quantity of transmitted light preferably comprise a plurality of sets, each set being formed by light-shielding areas and a plurality of combined light-transmitting areas arranged in a row, the light-transmitting areas having different width in the direction along the rotation direction of the rotary optical modulation plate. Mutually corresponding areas constituting each set are identical in terms of shape, size, transmittance, and arrangement order. The areas are arranged along the circle with the rotary shaft as a center, that is, along the rotation direction.

Those areas for example, include four areas 104a, 104b, 104c and 104d, the respective area width being D1, D2, D3, and D4, and the respective transmittance being T1, T2, T3, and T4. The area width satisfy the following relation: D1>D2>D3, and the area width D4 is selected according to the design. On the other hand, the transmittance of those areas satisfies the condition T1 (=T2=T3)>T4. For example, if T1 is set to 100 percent and T4 is set to 0 (zero) percent. Thus, the areas with transmittance T1, T2, and T3 are light-transmitting areas, and the area with transmittance T4 is a light-shielding area, that is, a non-transmitting area (it can be also called a nontransparent area). The area with a transmittance of 100 percent of the portions for regulating the quantity of transmitted light is the area where no film has been formed.

In the case of this configuration example, the arrangement orders of respective areas having those area widths are combined to obtain pattern areas 110 for regulating the quantity of transmitted light with an arrangement order of the area width of D1, D4, D2, D4, D3, D4 and those areas are considered as one area arrangement set. Thus, six areas constitute one area arrangement set in which nontransparent (T4) areas (width D4) are sandwiched one by one between other two areas with different area width. Those pattern areas 110 for regulating the quantity of transmitted light are arranged, in a plurality of sets, along the circumference around the central axis of the transparent disk 102. In the configuration example, shown in FIG. 4(A), there are three such combination arrangements. Because the area widths D1, D2, D3 are thus different, if the rotation speed of the rotary optical modulation plate is constant, the light transmitted through each area becomes the optical modulation signals of different duration.

The areas 104a, . . . , 104d may be substantially fan-like areas shown partially as an example in FIG. 4(B) or may be the areas of a shape bounded by two diameters of an arc of one circle and an arc of another circle, those two circles being concentric; such areas are partially shown as an example in FIG. 4(C).

Thus, three or more areas of mutually different width sandwich one by one the nontransparent areas and form an arranged set of pattern areas 110 for regulating the quantity of transmitted light (that is, an area arrangement set). Therefore, the arrangement order thereof and area shape are merely a matter of design.

The above-described rotary optical modulation plate 100 modulates the light generated from the light source 120 such as a light-emitting element. In the present configuration example, the modulation is demonstrated as a difference in the duration of the transmitted light. During rotation of the rotary optical modulation plate 100, the light from the light source 120 passes through the rotary optical modulation plate and is converted into an optical modulation signal L. This signal L is an analog signal. The optical modulation signal is received by a photoelectric conversion unit 122 such as a light receiving element and a photoelectric conversion signal V is generated. This signal V is an analog signal. Another light source, for example, a light-emitting diode can be used as the light-emitting element, and another optical detection device such as a photodiode can be used as the light receiving element. The size of the light-emitting surface and light-receiving surface in the light-emitting diode or photodiode is of an order of micrometers. Therefore, the set positions thereof can be selected within a wide range in the radial direction of the rotary optical modulation plate. As a result, the degree of freedom in designing the measuring instrument is increased.

The measurement unit 200 will be described below. The measurement unit 200 is provided inside the housing 10. The measurement unit is a device for converting the photoelectric conversion signal V obtained by conversion from the optical modulation signal generated in the optical modulating section 100 into an electric pulse signal P. This signal P is a digital signal. The measurement unit 200 comprises the above-described light-emitting element 120 and light-receiving element 122 disposed opposite each other so as to sandwich the optical modulating section 100 therebetween, a pulse forming circuit 210, and a microcomputer (µC) 220.

The pulse forming circuit 210 is a circuit for converting the photoelectric conversion signal V corresponding to the optical modulation signal and inputted from the light receiving element 122 into an electric pulse signal P.

Figure 5:
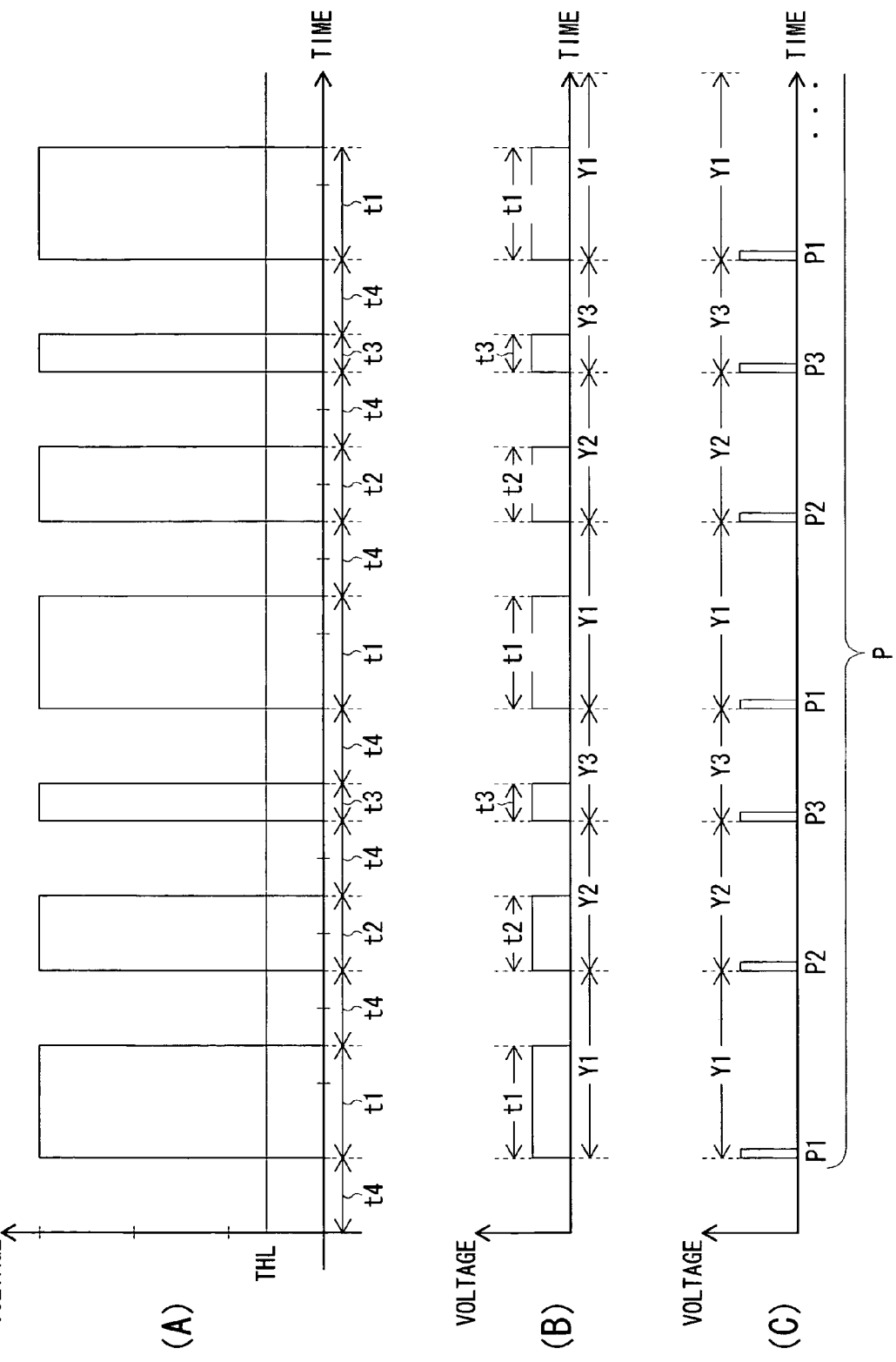
FIGS. 5(A), (B), and (C) are signal waveform diagrams for explaining an example of the process for converting photoelectric conversion signals from the optical modulating section constituting the length measuring instrument in accordance with the present invention into electric pulse signals.

The configuration and operation of the pulse forming circuit 210 itself are well known and the detailed explanation thereof is herein omitted. The electric pulse signal formation process will be described below in a simple manner with reference to FIG. 5.

FIGS. 5(A), (B), and (C) are signal (or pulse) waveforms for explaining this conversion process. In each figure, time is plotted against the abscissa and the voltage amount of the signal (or pulse) is plotted in arbitrary units against the ordinate.

FIG. 5(A) is a signal waveform diagram showing an example of photoelectric conversion signals V obtained when the optical modulating section 100 is used, this unit having portions for regulating the quantity of transmitted light with the above-described area widths D1, D2, D3, and D4. Those photoelectric conversion signals V have a certain rise time (front edge) and fall time (rear edge), but are substantially rectangular signals or signals with a waveform close to a rectangular one. In the figure, the duration of the photoelectric conversion signals corresponding to the light transmitted through areas with a width of D1, D2, D3, and D4 is denoted by t1, t2, t3, and t4.

Those photoelectric conversion signals V are input into the pulse forming circuit 210. In the pulse forming circuit 210, the photoelectric conversion signals V are clipped or limited by the preset threshold voltage (THL: threshold level). Then, if necessary, the waveform thereof is shaped and the sequence of rectangular signals shown in FIG. 5(B) is generated. This sequence of rectangular signals, as described hereinabove, has a duration width t1, t2, and t3 corresponding to the duration of the optical modulation signals obtained when the light is transmitted through the areas with different width. In the configuration example explained herein, the relationship t1>t2>t3 is valid. Furthermore, similarly, the time intervals Y1, Y2, and Y3 between the rises (front edges) in the sequence of rectangular signals also differ according to the duration of optical modulation signals, and the following relationship is valid: Y1>Y2>Y3.

After differentiation at the front edges thereof and optical pulse shaping, those rectangular signals are generated as electric pulse signals. Each pulse of the electric pulse signals thus obtained is denoted by P1, P2, and P3. The time interval between the pulses in the sequence is Y1, Y2, and Y3. The pulse train pattern of the electric pulse signals generated with such time intervals is shown in FIG. 5(C).

As for the above-mentioned differentiation, if the durations t1, t2, and t3 are short and the rectangular signals shown in FIG. 5(B) act substantially as pulse signals, the aforementioned differentiation processing becomes unnecessary.

If the pulse train pattern shown in FIG. 5(C) is considered as a pattern obtained in the forward rotation of the rotary shaft 20, then when the rotation of the rotary shaft is reversed, the pulses P1, P2, and P3 will be generated in the reverse order, that is, P1, P3, P2, and P1, and the durations will be also inverted to Y3, Y2, and Y1. The pulse train pattern in this case becomes a pattern inverted with respect to the pattern during forward rotation. Therefore, the forward and reverse rotation of the rotary shaft can be detected by observing this pulse train pattern.

In the case of the above-described configuration example, a correlation is set between the count in the pulse counter unit 236 and the draw-out amount of the measuring belt 30. For example, if the measuring belt 30 is drawn out by 1 cm, the rotary shaft 20 makes one turn. In this case, one turn of the rotary shaft 20 corresponds to a rotation angle of 360 degrees of the rotary optical modulation plate 100. Therefore, the rotation angle corresponding to a draw-out quantity of 1 mm is substantially 36 degrees. If a total of three sets, each set comprising the above-described area widths D1, D2, D3, and D4 are arranged in a center with a rotation angle of 36 degrees, then a correlation can be provided such that nine pulses P1, P2, P3, P1, P2, P3, P1, P2, P3 will be equivalent to a draw-out quantity of the belt of 1 mm. The relationship between the number of pulses and the draw-out quantity obviously may be different from the above-described relationship and this relationship is merely a design feature.

Figure 6:
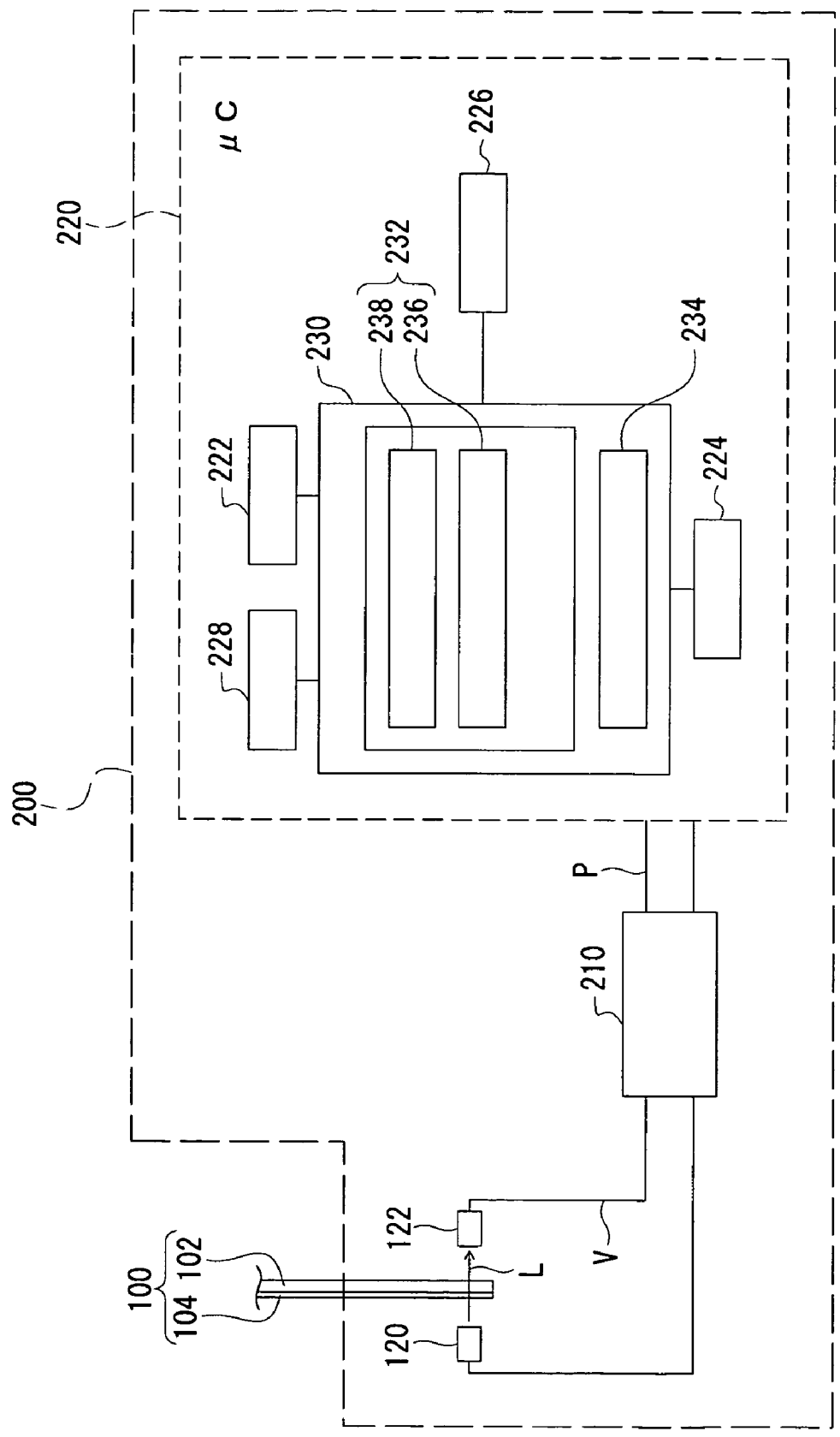
FIG. 6 is a view for providing explanation of a configuration example of the length measuring instrument in accordance with the present invention, in particular, the functions of the CPU.

The electric pulse signals P formed in the above-described manner are supplied to the microcomputer 220. The microcomputer 220 will be explained hereinbelow with reference to FIG. 6.

The microcomputer 220 is well known to comprise a central processing unit (CPU) 230, a storage device 222 comprising a ROM accommodating an operation processing program and a RAM storing the input data or processing results in a readable form, an input unit 224 for inputting various input commands, a display section 226 for displaying the input commands, processing results and other required information, and a control unit 228 for conducting control necessary for the operation of the microcomputer.

The input unit 224 comprises various control function buttons of push-button type or external connection terminals for inputting the programs or external information. For example, as shown in FIG. 3, the control function buttons can include a switch button S for turning the power source ON and OFF, a clear button C, a determination button D, a mode selection button M, and a setting button ((+) button and (−) button) B for text, numbers, or symbols.

The storage device 222 stores in advance the selected mode information, the information on the required text, numbers, or symbols, information on the reference pulse train pattern which serves as a reference for deciding whether the rotary shaft 20 rotates in the forward or reverse direction, information for control commands, and other information. Examples of mode information include personal information such as the name, age, and gender of the person conducting measurements, the year, month, and day the measurements are conducted, the name of the part which is the object of measurements, the display method, measurement start, and the like. The display method can be in measurement units, unit measurement data, comparative data, history data, differential values, and the like. It goes without saying that the type of information and the display method are merely the design issues.

Further, the relationship between the count in the pulse counting section 236 and the draw-out quantity (length units) for the reference point of the length of the measuring belt is investigated in advance. The correspondence between this count and the draw-out length is set as a table and stored in advance in the storage device 222 in a readable format. In this case, the length units are preferably millimeters.

The CPU 230 functions as a length determination unit 232 and a display control unit 234. The display control unit controls the display of the required information in the display section 226 according to a command from the input unit or in response to the internal processing results. The display control unit 234, for example, conducts processing for conducting display in the display section 226 in the mode selected in the input unit 224.

The length determination unit 232 functions as a pulse counting section 236 and forward/reverse rotation determination unit 238.

Figure 7:
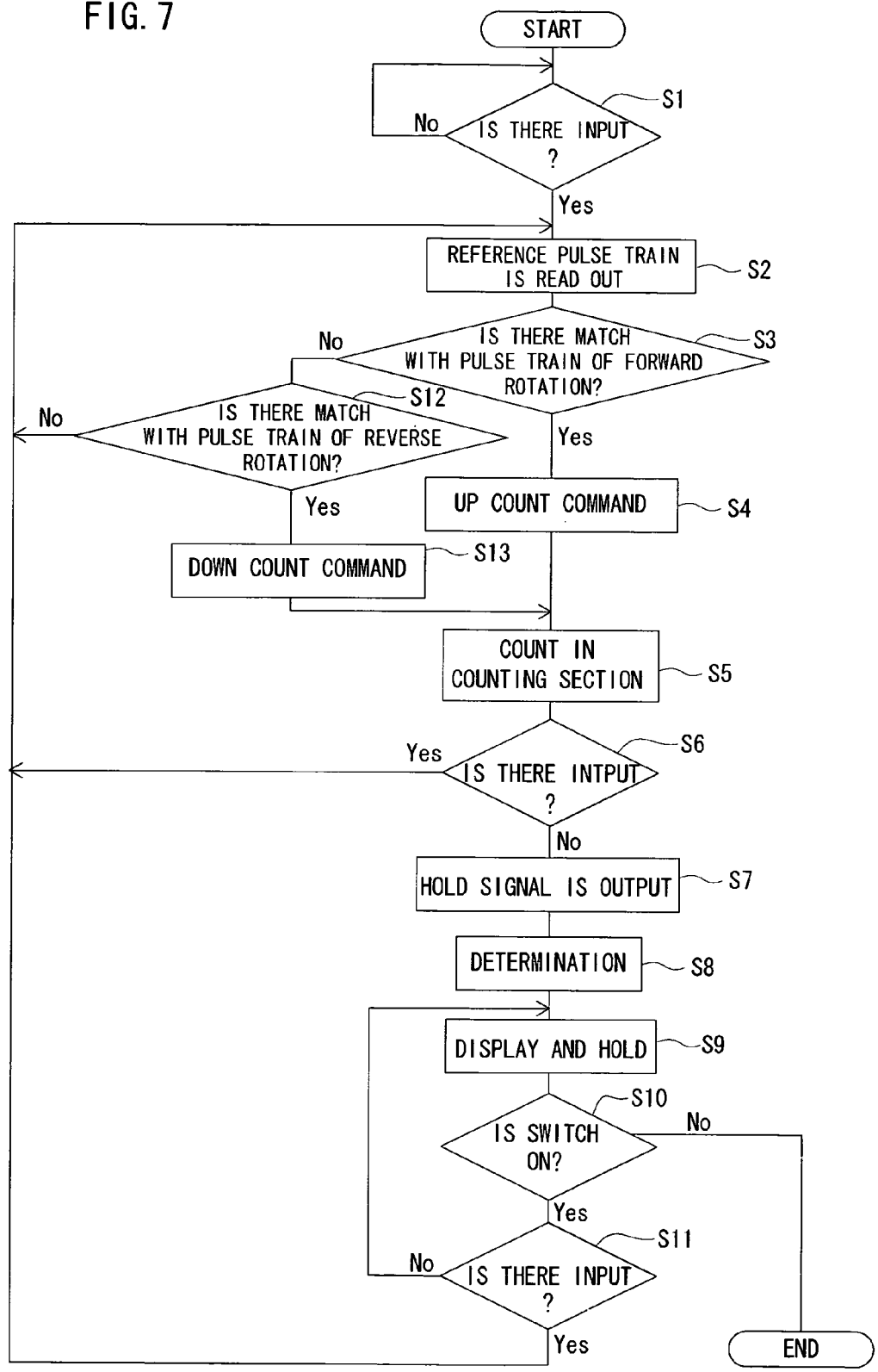
FIG. 7 is a flow diagram for providing explanation for the sequence of operations of the CPU shown in FIG. 6.

The operation of the microcomputer (referred to hereinbelow in an abbreviated form as μC) will be explained below with reference to the operation flow chart of the length determination unit 234 shown in FIG. 7.

A switch S is switched on and the device is set into an operation mode. The measurement position is selected and displayed by the operation of the mode selection button M, and then the measurement mode is selected and the measurements are started. If in this state, the measuring belt 30 is drawn out and an electric pulse signal P is input from the pulse formation circuit 210 into the μC 220, this pulse signal P is input into the forward/reverse rotation judging section 238 and pulse counting section 236. The forward/reverse rotation judging section 238 and pulse counting section 236 verify whether the pulse signal P has been input (S1). When the pulse signal P has been input, the forward/reverse rotation judging section 238 reads out the reference pulse train pattern (sometimes simply referred to hereinbelow as a reference pattern) from the storage device 222 (S2). The pulse train pattern of the inputted pulse signal P is compared with the reference pattern of the direct rotation that was read out (S3). If a decision is made that the pulse train pattern of the inputted pulse signals matches the reference pattern of the forward rotation, a command is issued to add a count (count up) in the pulse counter unit 236 (S4). In response to this addition command, the pulse counter unit 236 successively counts each pulse of the electric pulse signals P in the order of input thereof (S5).

If the drawing of the measuring belt 30 is stopped in a slack-free tensioned state thereof, the continuous input of the electric pulse signals is stopped. After the forward/reverse rotation determination unit 238 has confirmed (S6) that the input of the electric pulse signals P has stopped, a hold signal to stop the addition counting is output from the forward/reverse rotation determination unit 238 to the pulse counting section 236 (S7). The pulse counting section 236 holds the number of pulses that has been heretofore counted. This count becomes the measurement result of the draw-out length of the measuring belt 30, that is, the measurement data of the part being measured. At the same time, this hold signal is also supplied to the display control unit 234, and the display control unit 234 reads the value of the length corresponding to the aforementioned count from the storage device 222 by using the count held in the pulse counting section 236 as an address. The display control unit 234 displays the read-out length as the measurement data of the part that is measured on the display section 226.

The count is determined (S8) by the operation of the determination button D of the input unit 224 and this value is held in a displayed state in the display section 226 and the displayed data is recorded in a readable form in the storage device 222 (S9).

Thus, if a decision is made that the rotary shaft is rotated forward by the measuring belt which is drawn out, the number of electric pulses corresponding to the draw-out quantity of the belt is counted. The count is determined and displayed in a numerical form as the length of the drawn-out measuring belt.

Then, it is checked whether the power source switch of the measuring instrument is ON or OFF (S10). If the switch of the measuring instrument is in the ON period, a decision is again made as to whether the inputted pulse train is present (S11). If the pulse train is present, the processing flow returns to step S9 and the displayed state is further held. When the power source switch is OFF, measurements with the measuring instrument are completed.

When a decision is made in step S11 that there is a new pulse train, the processing flow returns to step S2.

When the measuring belt 30 has not been tightly applied and wound around the part being measured, or when part of the drawn-out belt is loose, the rotary shaft drive unit 40 operates automatically, rotates the rotary shaft 20 in reverse and rewinds the belt, so that the belt assumes a tight tensioned state. In this case the forward/reverse rotation determination unit 238 makes a decision that the shaft rotates in reverse.

Thus, when the comparison results of step S3 lead to a decision that the reference pattern of forward rotation is no matched, the pulse train pattern is compared with the reference pattern of the reverse rotation (S12). If a decision that the reference pulse train pattern of reverse rotation is matched is made in this step S12, then a subtract count command is issued (S13) from the forward/reverse rotation determination unit 238 to the pulse counting section 236, the processing flow advances to the nest step S5, and the pulse counting section 236 conducts a subtraction (down) count from the number of pulses that have heretofore been counted (S5). The step S6 and the subsequent steps are the same as described hereinabove.

Thus, the results of the addition and subtraction counting in the pulse counting section 236 are held in a state in which they were read out from the storage device 222 and numerically displayed on the display 226. At the same time, they are recorded in the storage device 222 as the measurement data of the part that is measured (S9).

Thus, in accordance with the decision relating to the forward/reverse rotation in the forward/reverse rotation determination unit 238, the pulse counting section 236 either conducts the addition counting or conducts the subtraction counting from the addition counting and determines and outputs the final count. This final count is determined and displayed as the measurement result, that is, the draw-out length of the measuring belt 30.

When the measurement are wished to be restarted or terminated in the course of the measurement process, the display can be instantly cleared in a well-known manner by operating a clear button C.

Further, the guiding unit of the measuring belt will be explained below with reference to FIG. 2(A), FIG. 2(B), and FIG. 8. The length measuring instrument in accordance with the present invention preferably comprises a guiding unit 60 with the configuration shown in FIG. 8. The guiding unit 60 is preferably provided on the outer side surface of the housing 10 having the prescribed length, preferably, on the top surface 54 of the housing 10. The guiding unit 60 comprises a push bar 52 that applies pressure to the top surface 54 of the housing and the belt from the outer side and a latching section 50 provided in the distal end portion. The push bar 52 is designed to prevent the belt from loosening, and the necessary number of such bars may be provided according to the design.

The measuring belt 30 drawn out from a draw-out opening 14 of the housing 10 is guided by the guiding unit 60 to the distal end portion thereof, and a latching tool 32 is latched with the latching section 50, thereby cueing the measuring belt 30. The latching tool 32 and latching section 50 may be formed from any material and have any structure, provided that the structure thereof allows them to be latched with each other in a releasable manner, and they are merely the design features.

Alternatively, in the length measuring instrument in accordance with the present invention, as shown in FIGS. 2(A) and 2(B), a guiding unit 70 joined to the outer surface of the housing 10 is preferably provided. This guiding unit 70 is formed to be a rod-like or bar-like body 72 with the prescribed length and one end section 74 of the rod-like body 72 is so provided that the rod-like body 72 can be freely rotated in the housing 10 or held in the desired rotation position. The fixing method thereof can use a friction force or a ratchet system, as in well-known structures, and detailed explanation thereof is omitted.

In the case of this guiding unit 70, one end section 74 of the rod-like body 72 may be provided by mounting on the end of the top surface 54 of the housing 10. Furthermore, the latching section 80 is provided at the distal end section 76, which is the free end of the rod-like body 72. The longitudinal sectional view in FIG. 2(B) clearly shows, that the latching section 80 has a structure comprising an opening 80a for drawing out the measuring belt 30 and an opening 80b allowing the latching tool 32 located at the distal end of the belt to be passed through for latching. Furthermore, if desired, the rod-like body 72 may be provided with a push bar 78 in the same manner as the guiding unit 60 explained with reference to FIG. 8.

When the guiding unit 70 is not in a state of use, it is rotated toward the top surface 54 of the housing 10 and accommodated above the top surface. For example, a convex section 82 for engagement with the latching section 80 of the rod-like body 72 can be provided, and the latching section 80 can be engaged with the convex section 82, thereby fixing the rod-like body 72 so that it can be latched.

With the above-described configuration in which the length measuring instrument is provided with the guiding unit 60 or 70, the distal end section of the guiding unit can be considered as a reference point for a draw-out length of the belt 30. This reference point can be set in the position separated from the draw-out opening 14 of the housing for drawing out the measuring belt. During measurements, the distal end section of the guiding unit 60 or 70 is brought into contact with the part 90 which is to be measured. As a result, the belt 30 is strongly tensioned, without being loose, by the action of the above-described rotary shaft drive unit 40 and tightly applied to the outer periphery of the part 90 being measured. Furthermore, the intermediate portion of the belt between the distal end section of the guiding unit and the rotary shaft 20 is also strongly tensioned without a loose.

Figure 8:
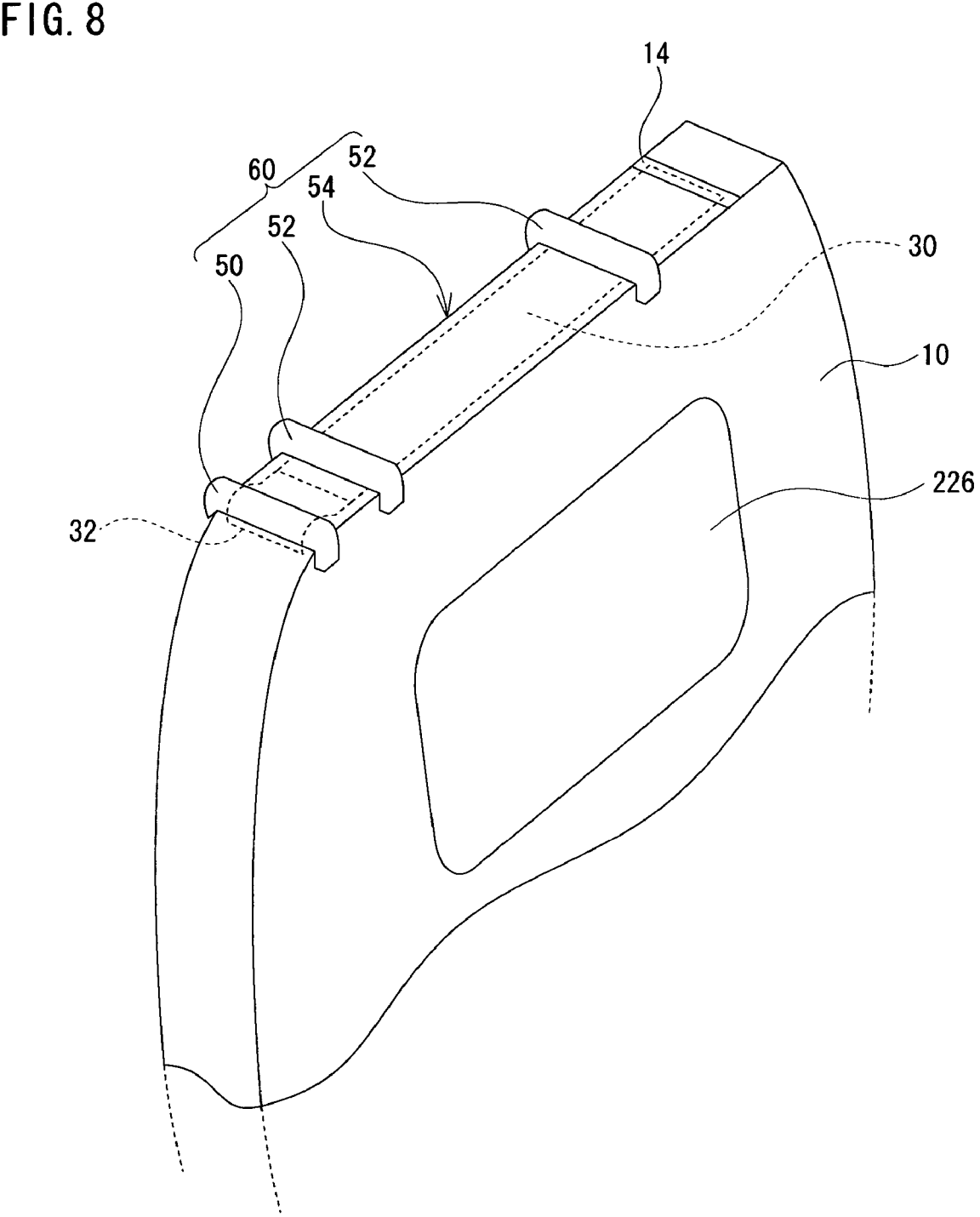
FIG. 8 is a partial perspective view for providing explanation of another configuration example of the guiding unit constituting the length measuring instrument in accordance with the present invention.

With the guiding unit 60 or 70 shown in FIG. 8, FIG. 2(A), and FIG. 2(B), the measuring belt 30 is cued when the latching tool 32 of the measuring belt 30 is engaged with the latching section 50 or 80 of the guiding unit. As has already been explained hereinabove, the pulse counting section 236 of the length measurement unit 232 is adjusted so that the length display in the display section 226 is zero when the belt is in this initially drawn-out state.

The above-described configurations of the two guiding units 60 and 70 are merely the preferred examples and are in no way limiting. Therefore, any other configuration may be used, provided that the above-described object can be attained.

The explanation above was conducted with respect to the preferred configuration example, but the present invention can provide the effect similar to that obtained in the above-described configuration example, even if it is changed or modified in a variety of ways.

Figure 9:
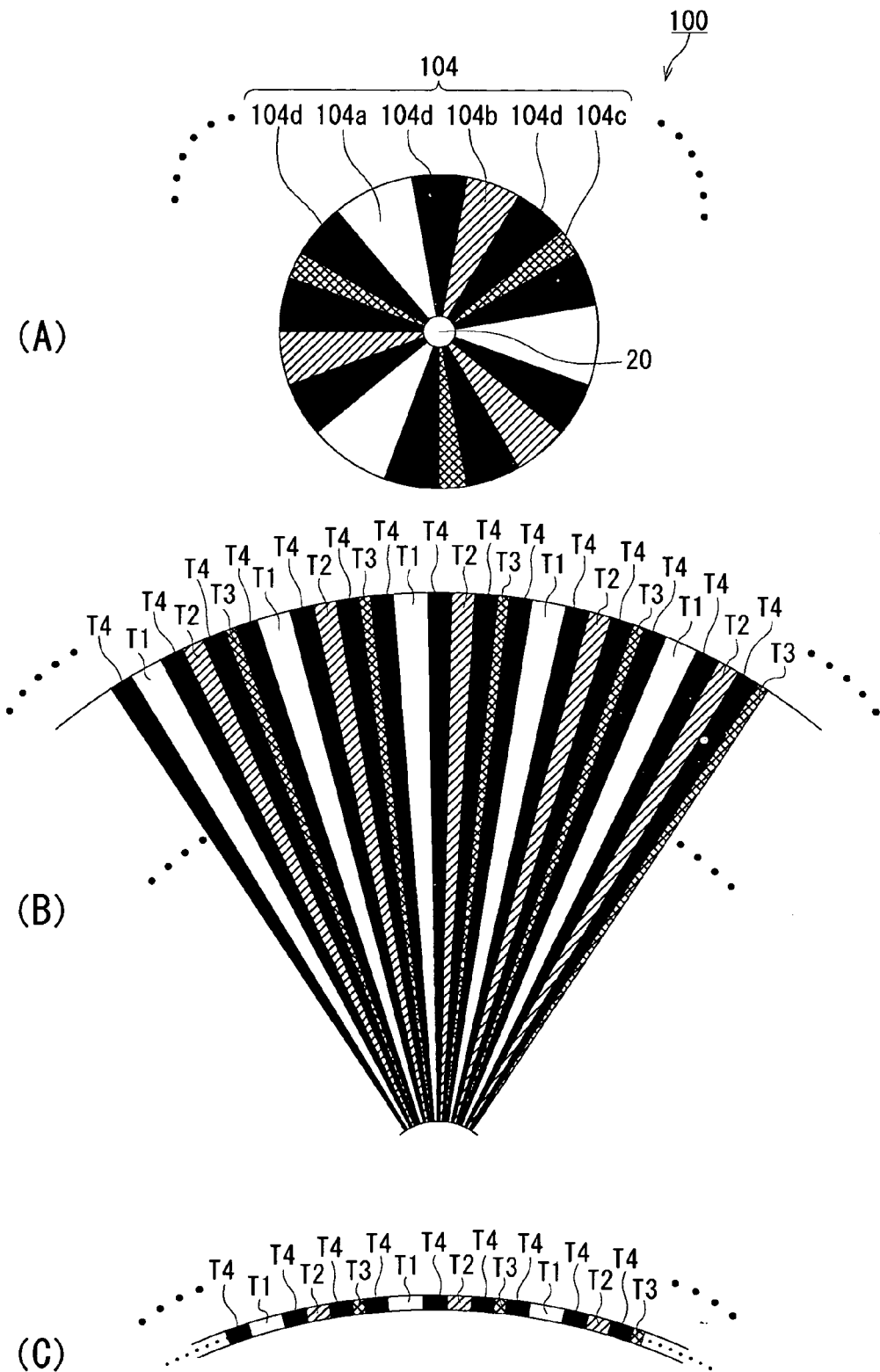
FIGS. 9(A), (B), and (C) are views for providing explanation of another configuration example of the optical modulating section constituting the length measuring instrument in accordance with the present invention.

For example, as shown in FIGS. 9(A), (B), and (C), the transmittance T1, T2, T3, and T4 of the areas 104a, 104b, 104c, and 104d of the portions 104 for regulating the quantity of transmitted light satisfy the relation: T1>T2>T3>T4, that is, a certain difference can be provided between the transmittance values. For example, T1 can be 100 percent, T2—70 percent, T3—40 percent, and T4—0 (zero) percent. In other aspects, the configuration is identical to the configuration explained with reference to FIG. 4(A), (B), and (C).

Figure 10:
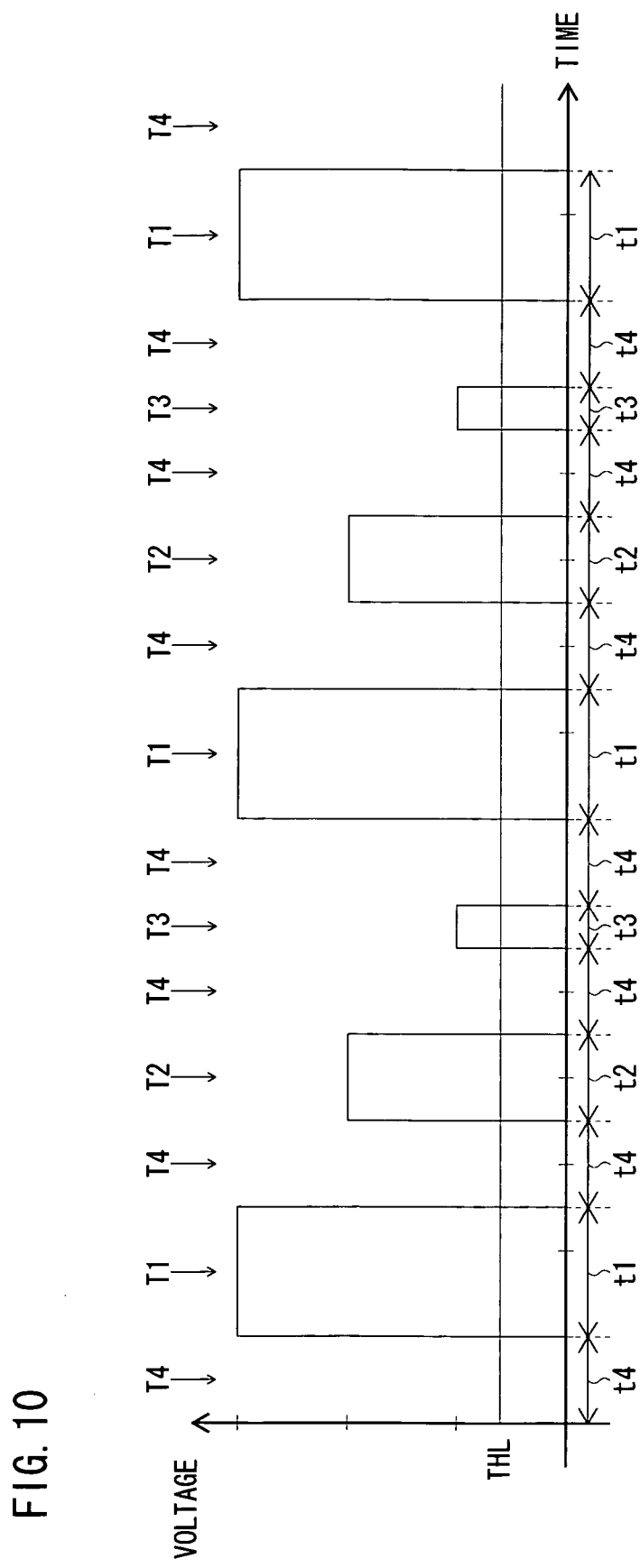
FIG. 10 is a signal waveform diagram for explaining another example of the process for converting photoelectric conversion signals from the optical modulating section constituting the length measuring instrument in accordance with the present invention into electric pulse signals.

FIG. 10 is a signal (or pulse) waveform diagram explaining he conversion process in the case a difference is provided between the transmittance values. In the figure, the abscissa is a time axis, and the value of the signal (or pulse) voltage is plotted in arbitrary units on the ordinate. The difference with the signal waveform that was explained with reference to FIG. 4(A) is in that this signal is a photoelectric conversion signal of light intensity corresponding to the transmission. In this case, for example, as was explained with reference to FIGS. 5(A) to 5(C), when those photoelectric conversion signals are clipped or limited by a fixed threshold voltage, subsequent processing of conversion thereof into pulses is identical to that explained with reference to FIGS. 4(B) and (C), and detailed explanation thereof is omitted.

However, a configuration can be also used in which the light intensity shown in FIG. 10 is replaced with the number of pulses within a duration interval (can be also referred to as "duration interval width") of the photoelectric conversion signal and the judgment relating to the forward or reverse rotation is made based on the difference in the number of pulses.

Figure 11:
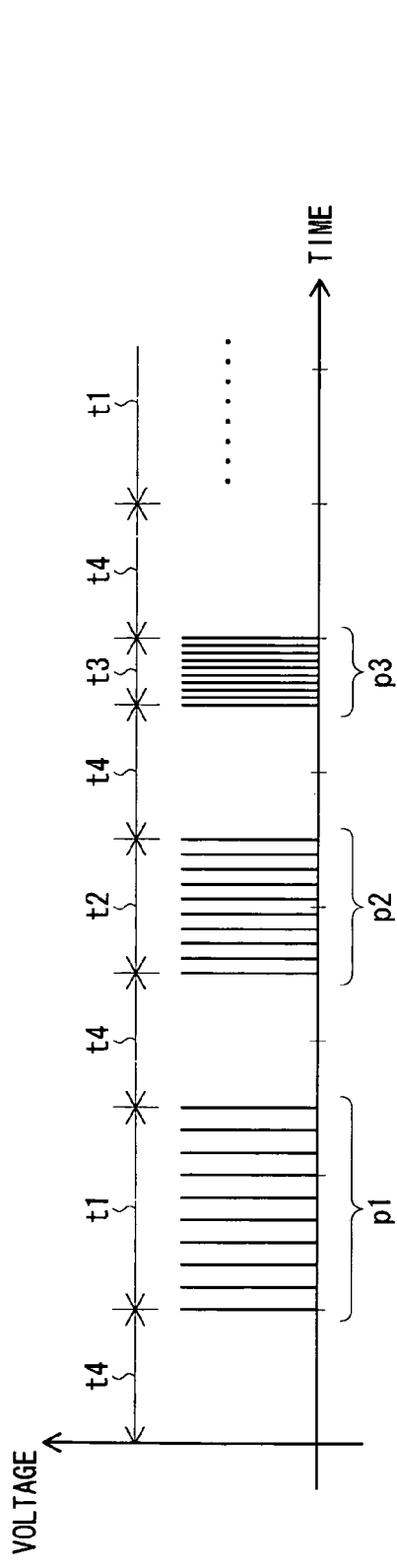
FIG. 11 is a view for explaining a pulse generation state for explaining another example of the process for converting photoelectric conversion signals from the optical modulating section constituting the length measuring instrument in accordance with the present invention into electric pulse signals.

This aspect will be explained in a simple manner with reference to FIG. 11. In the figure, the abscissa is a time axis, and the value of the voltage is plotted in arbitrary units on the ordinate. The figure illustrates the pulse generation state. Thus, for example, when the duration interval widths of the photoelectric conversion signals are different, if the number of pulses generated within the duration interval and corresponding to the entire photoelectric conversion signal is set to 10 with equal spacing between the pulses, then equidistantly spaced pulse trains p1, p2, and p3 corresponding to the length to time intervals of respective photoelectric conversion signals will be generated. As a result, the decision on the forward or reverse rotation can be also made based on the difference in the patters of time intervals of individual pulses in the pulse trains. For such a conversion to pulses, from the standpoint of hardware, the pulse formation circuit 210 may be configured so that after the respective duration intervals t1, t2, and t3 have been set or measured in advance, those duration intervals t1, t2, and t3 are be divided, for example, into 10 equal parts and one pulse is generated for each of the 10 divided intervals. Creating such a configuration is obvious to a person skilled in the art and detailed explanation thereof is herein omitted.

Alternatively, by contrast with the above-described configuration of adjustment pattern areas of the optical modulating section, which was explained with reference to FIGS. 4(A) to 4(C) and 9(A) to 9(C), the light transmission quantity adjustment areas with different transmittance may be formed so as to have identical width in the rotation direction. In this case, the photoelectric conversion signals corresponding to each area have different light intensity levels, but the respective duration interval widths are the same.

Figure 12:
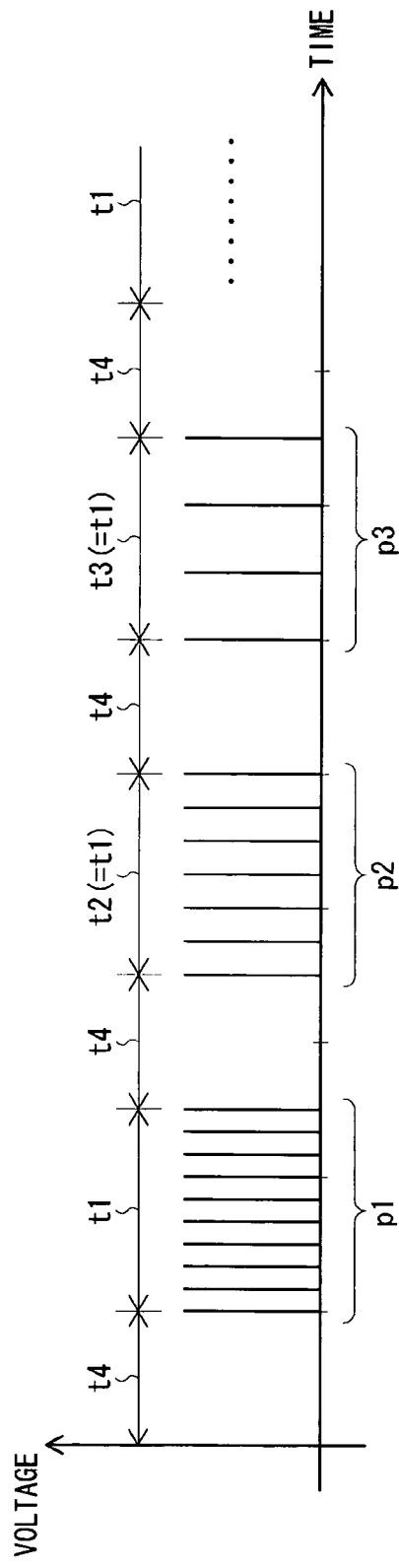
FIG. 12 is a view for explaining a pulse generation state for explaining yet another example of the process for converting photoelectric conversion signals from the optical modulating section constituting the length measuring instrument in accordance with the present invention into electric pulse signals.

This aspect will be explained in a simple manner with reference to FIG. 12. In the figure, the abscissa is a time axis, and the value of the voltage is plotted in arbitrary units on the ordinate. The figure illustrates the pulse generation state.

In this case, if we assume that the number of pulses corresponding to the value of the light intensity level is generated, then the generation time intervals between the pulses generated within the same retention time (t1=t2=t3) in the photoelectric conversion signals will be different. The forward or reverse rotation can be also judged by the difference between the time intervals of those pulses. In order to convert to those pulses, the number of pulses generated for each light intensity level is determined in advance, for example, as 10, 7, or 4, and the pulse formation circuit 210 may be configured so that one pulse is generated for each interval obtained by dividing the duration interval by the number of pulses generated for each level after the respective light intensity level and duration interval has been measured. Because the duration interval is constant, the number of pulses in pulse trains p1, p2, and p3 generated in respective duration intervals differ. Therefore, the generation time intervals between the individual pulses in the pulse trains p1, p2, and p3 will be different. In this case, the forward/reverse rotation can be judged from the difference between the patterns of generation time intervals of the pulses. Forming such a configuration is obvious to a person skilled in the art and detailed explanation thereof is herein omitted.

The explanation above was conducted with reference to an example of a spiral spring as a rotary shaft drive unit 40, but a configuration using an electric motor instead of the spring can be also used.

Figure 13:
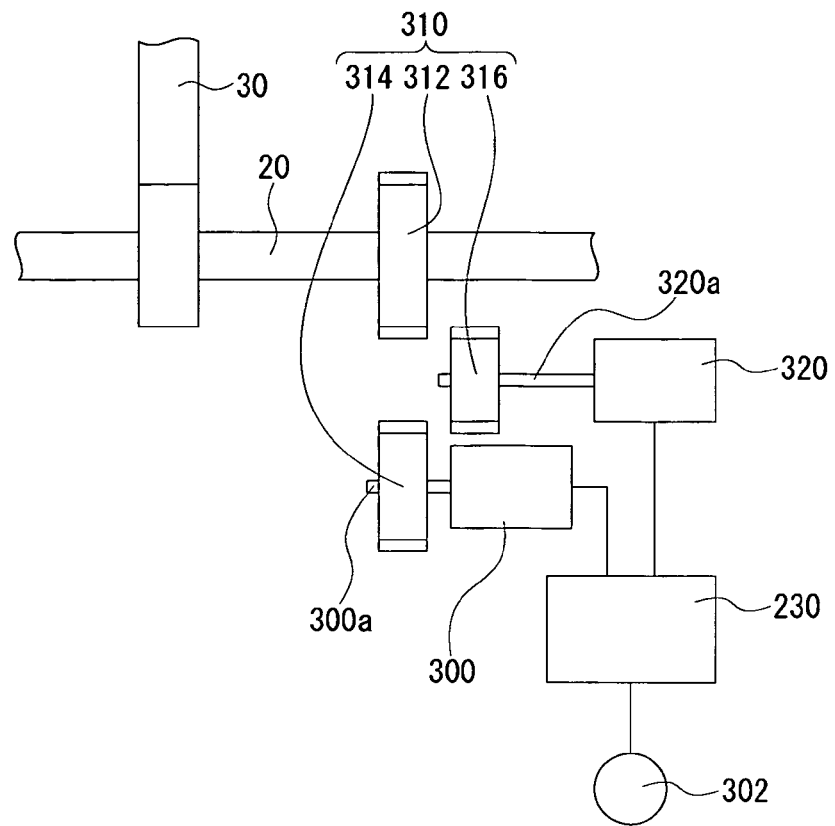
FIG. 13 is a schematic drawing for explaining another configuration example of the rotary shaft drive unit constituting the length measuring instrument in accordance with the present invention into electric pulse signals.

This aspect will be explained with reference to FIG. 13. FIG. 13 is an explanatory drawing illustrating the connection relationship between an electric motor and a rotary shaft. In this case, for example, there are provided a power transmission mechanism 310, for example, comprising a set of gears 312, 314, and 316 that can engage the rotary shaft 20 with electric motor 300 so that they can be disengaged, and a motor switch 302 for ON/OFF switching the electric motor 300. The first gear 312 is provided on the rotary shaft 20. The second gear 314 is provided on the motor shaft 300a of the electric motor (also called "electrically operated motor"). The third gear 316 is so provided that it can be inserted between the first and second gears and engaged therewith. The drive for this insertion is provided according to ON/OFF operation of the motor switch 302 by the control drive unit 320 via the CPU 230.

The motor switch 302 is provided on the full-surface panel of the housing and configured to enable the operation of the electric motor 300 via the CPU 230. When the motor switch 302 is set to OFF, that is, when the electric motor is in a passive state, the power transmission mechanism located between the electric motor and rotary shaft 20 is disengaged from the rotary shaft. The measuring belt 30 is drawn out for measurements in this state. When the measuring belt 30 is rewound to pull out a slack of the measuring belt 30, the motor switch is turned ON, the power transmission mechanism 310 is linked to the rotary shaft, and the electric motor 300 is actuated. Due to the actuation of the electric motor 300, the rotary shaft 20 is rotated in reverse and when the measuring belt 30 is tensioned, the actuation of the electric motor may be terminated.

With this method, for example, the end of electric pulse signals generation during the above-described reverse rotation of the rotary shaft is detected. In response to this detection, a stop signal for stopping the actuation of the electric motor is outputted to the electric motor from the forward/reverse rotation judging section 238 and the electric motor may be stopped. Alternatively, if the measuring belt 30 is tensioned without a slack, then a negative load is applied, as it is known, to the shaft of the electric motor by the tensile force of the belt 30. A configuration may be employed in which this negative load is detected as a negative load current and the electric motor is thus stopped.

In the above-described preferred embodiment, the optical modulation was explained with respect to a configuration example in which the rotary optical modulation plate 100 was directly fixed to the rotary shaft 20, but this configuration is in no way limiting.

Figure 14:
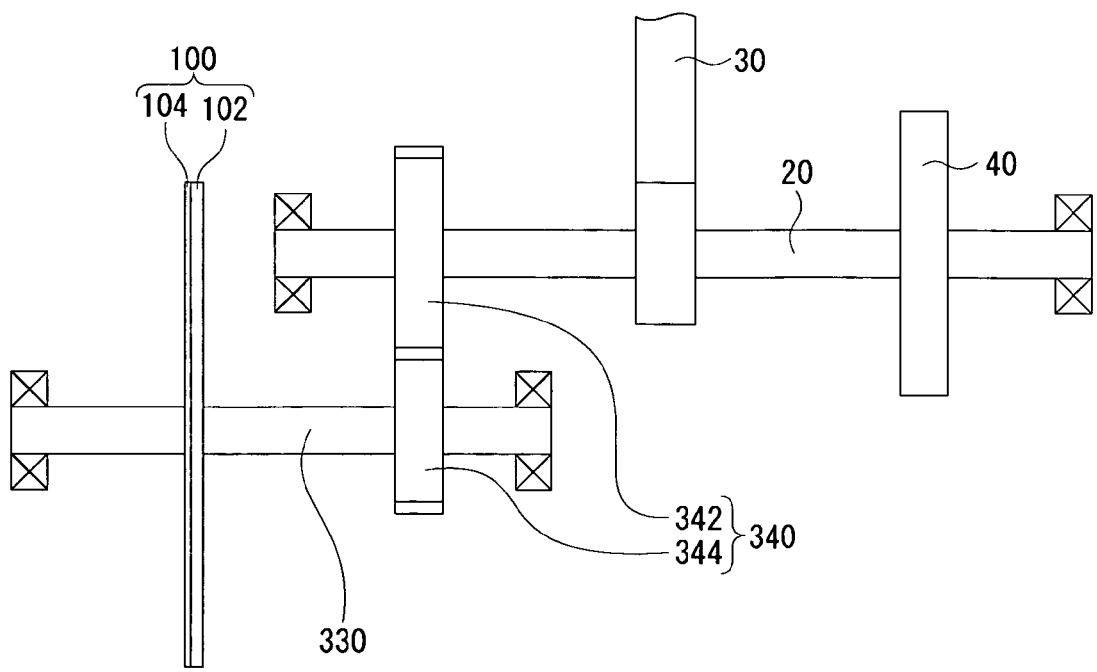
FIG. 14 is a schematic drawing for explaining another configuration example of the rotary shaft drive unit constituting the length measuring instrument in accordance with the present invention into electric pulse signals.

This aspect will be explained in a simple manner with reference to FIG. 14. FIG. 14 explains the linking relationship of the optical modulating section, that is, the rotary optical modulation plate 100 and rotary shaft 20. For example, a rotary shaft (referred to as a modulation plate rotary shaft or second rotary shaft) 330 for fixing the rotary optical modulation plate 100 is provided separately from the rotary shaft 20. Between the above-described rotary shaft 20 and the second rotary shaft 330, the rotary shaft 20 and the second rotary shaft 330 are linked by a rotation transmission mechanism 340 using a combination of two or three gears. For example, the first gear 342 is provided on the rotary shaft 20, and the second gear 344 engageable with the first gear 342 is provided on the second rotary shaft 330. At this time, a configuration may be used such that a diameter of gears and the number of gears is adjusted and the second rotary shaft 330 is rotated through any prescribed number of turns, for example, 2 to 3 or more turns, correspondingly to one turn of the rotary shaft 20. If such a configuration of the rotation transmission mechanism 340 is used, the rotation angle of the rotary shaft 20 rotating according to a very small draw-out quantity of the measuring belt 30 can be enlarged in the second rotary shaft 330 to a double, triple, or larger rotation angle. The above-described light transmission quantity adjustment sections 104 can be arranged and formed over the area within the range of the rotation angle that was thus enlarged. Therefore, the degree of freedom in designing the correspondence relationship between the measuring belt 30 and the number of generated electric pulse signals P is increased.

Figure 15:
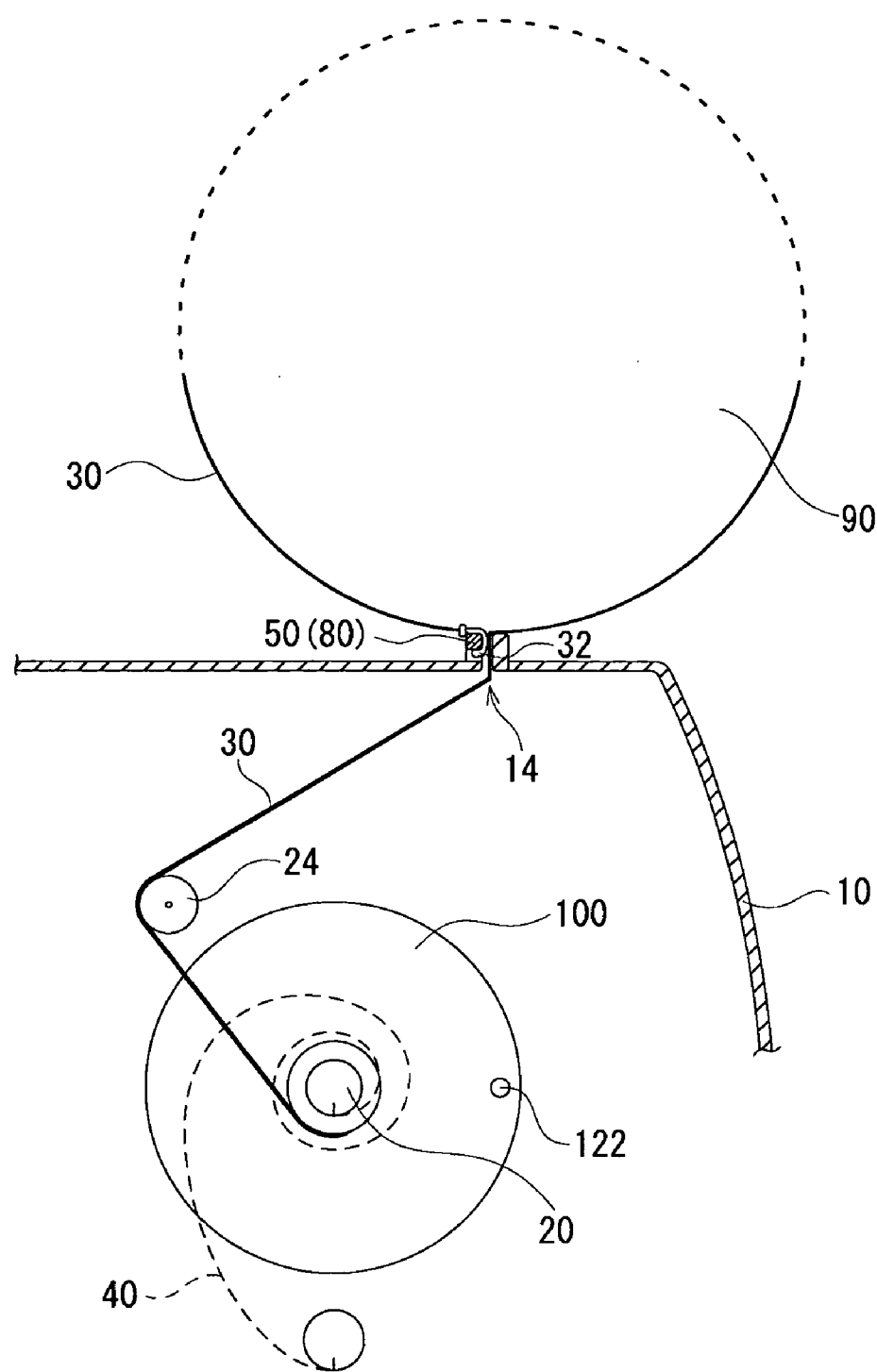
FIG. 15 is a partial perspective view employed for explaining yet another configuration example of the guiding unit constituting the length measuring instrument in accordance with the present invention.

Further, as shown in FIG. 15, instead of providing the above-described guiding unit 60 or 70, a latching section 50 or 80 may be provided at the housing 10 adjacently to the draw-out opening 14 for the measuring belt 30 in the housing 10. In this case, the distal end of the measuring belt 30 can be linked to the latching section 50 or 80 provided on the housing with the latching tool 32 thereof.

Further, the above-described configuration example was explained with reference to an example of measuring the circumferential length of the part being measured, but when both hands can be used, the length along the part, rather then circumferential length, can be also measured.

Furthermore, with the length measuring instrument of the present invention, data measured for each part are recorded in the recording unit 222 and the display in a desired mode can be conducted on the display section 226 by a command from the input unit 224. For example, the desired data display can be the display of history of measurement data of a specific part, combined display of measurement data for various parts, data indicating increase or degrease ratio of the measurement results relating to a specific part, and comparative data obtained by recording the ideal values for a specific part in advance and comparing the measurement values with the ideal values.

INDUSTRIAL APPLICABILITY

The length measuring instrument in accordance with the present invention is advantageously in the form of a small, lightweight, portable product suitable as an instrument for health control and the utilization value thereof is high.

The invention claimed is:

1. A length measuring instrument for measuring the length of a part being measured by the draw-out length of a measuring belt, comprising:
   a housing;
   a rotary shaft rotatably held inside said housing;
   the measuring belt wound around said rotary shaft so that one end portion thereof is fixed to the rotary shaft, comprising a latching tool on the other end portion, and causing said rotary shaft to rotate in the forward direction when the measuring belt is drawn out from the side of said other end portion to the outside of said housing;
   a rotary shaft drive unit provided inside said housing and rewinding the measuring belt by rotating said rotary shaft in the reverse direction;

an optical modulating section provided in communication with said rotary shaft and used for converting light from a light source into optical modulation signals;

a measurement unit provided inside said housing for converting said optical modulation signals into electric pulse signals, counting the number of said electric pulse signals, determining the draw-out length of the measuring belt from the counted number, and displaying the determined length as a measurement result;

a latching section provided outside said housing and capable of latching with the latching tool of said measuring belt; and a guiding unit having the prescribed length and formed on the outer side surface of said housing, wherein said measurement unit comprises said light source, a photoelectric conversion unit for converting said optical modulation signals into photoelectric conversion signals, a pulse formation circuit for converting said photoelectric conversion signals into electric pulse signals, a length determination unit for determining the draw-out length from the number of said electric pulse signals and outputting the determined length, wherein said length determination unit comprises a forward/reverse rotation judging section for deciding as to whether said rotary shaft rotates into forward direction or reverse direction from said electric pulse signals, and a pulse counting section that addition counts the number of said electric pulse signals when said forward/reverse rotation judging section decides that the rotation is in the forward direction, subtraction counts the number of said electric pulse signals when said forward/reverse rotation judging section decides that the rotation is in the reverse direction, and outputs the final count number obtained as a result of said addition counting and subtraction counting as said measurement result;

and wherein said guiding unit comprises a distal end section provided with said latching section, and the measuring belt that has been drawn out from said housing is guided till the distal end section is reached along said guiding unit, and said latching tool is latched with said latching section and cues the measuring belt.

2. The length measuring instrument according to claim 1, wherein said optical modulating section comprises a rotary optical modulation plate fixed to said rotary shaft, and said rotary optical modulation plate comprises a transparent disk and a plurality of portions for regulating the quantity of transmitted light arranged successively and adjacently on the surface of said transparent disk.

3. The length measuring instrument according to claim 2, wherein some of a plurality of said portions for regulating the quantity of transmitted light are light-shielding areas and the remaining part of a plurality of said portions for regulating the quantity of transmitted light are light-transmitting areas of different width in the rotation direction of said rotary optical modulation plate.

4. The length measuring instrument according to claim 2, wherein a plurality of said portions for regulating the quantity of transmitted light are light-transmitting areas with different light transmittances.

5. The length measuring instrument according to claim 1, wherein said optical modulating section is constituted as a rotary optical modulation plate provided directly or indirectly on the rotary shaft, and said rotary optical modulation plate comprises a transparent disk and a plurality of portions for regulating the quantity of transmitted light arranged successively and adjacently on the surface of said transparent disk.

6. The length measuring instrument according to claim 5, wherein some of a plurality of said portions for regulating the quantity of transmitted light are light-shielding areas and the remaining part of a plurality of said portions for regulating the quantity of transmitted light are light-transmitting areas of different width in the rotation direction of said rotary optical modulation plate.

7. The length measuring instrument according to claim 5, wherein a plurality of said portions for regulating the quantity of transmitted light are light-transmitting areas with different light transmittances.

8. The length measuring instrument according to any one of claim 1, wherein said light source is a semiconductor light-emitting element, said photoelectric conversion unit is a semiconductor light-receiving element, and said semiconductor light-emitting element and semiconductor light-receiving element are disposed opposite each other so as to sandwich said optical modulating section therebetween.

9. The length measuring instrument according to claim 1, wherein said rotary shaft drive unit is a spiral spring.

10. The length measuring instrument according to claim 1, wherein said rotary shaft drive unit is an electric motor.

11. The length measuring instrument according to claim 1, wherein said measurement unit further comprises a storage device for recording the measurement information such as a display mode and said measurement results in a readable form, a display section for displaying said measurement information, an input unit for selectively inputting a variety of commands instructing to select the displayed measurement information, determine the recording of measurement result, and clear the measurement information displayed in said display section, and a display control unit for controlling the display in said display section according to the command from said input unit.

12. A length measuring instrument for measuring the length of a part being measured by the draw-out length of a measuring belt, comprising a housing;

a rotary shaft rotatably held inside said housing;

the measuring belt wound around said rotary shaft so that one end portion thereof is fixed to the rotary shaft, comprising a latching tool on the other end portion, and causing said rotary shaft to rotate in the forward direction when the measuring belt is drawn out from the side of said other end portion to the outside of said housing;

a rotary shaft drive unit provided inside said housing and rewinding the measuring belt by rotating said rotary shaft in the reverse direction;

an optical modulating section provided in communication with said rotary shaft and used for converting light from a light source into optical modulation signals;

a measurement unit provided inside said housing, converting said optical modulation signals into electric pulse signals, counting the number of said electric pulse signals, determining the draw-out length of the measuring belt from the counted number, and displaying the determined length as a measurement result;

a latching section provided outside said housing and capable of latching with the latching tool of said measuring belt; and a guiding unit having the prescribed length and formed on the outer side surface of said housing, wherein said measurement unit comprises said light source, a photoelectric conversion unit for converting said optical modulation signals into photoelectric conversion signals, a pulse formation circuit for converting said photoelectric conversion signals into electric pulse signals, a length determination unit for determining the draw-out length from the number of said electric pulse signals and outputting the determined length, wherein said length determination unit comprises a forward/reverse rotation judging section for deciding as to whether said rotary shaft rotates into forward direction or reverse direction from said electric pulse signals, and a pulse counting section that addition counts the number of said electric pulse signals when said forward/reverse rotation judging section decides that the rotation is in the forward direction, subtraction counts the number of said electric pulse signals when said forward/reverse rotation judging section decides that the rotation is in the reverse direction, and outputs the final count number obtained as a result of said addition counting and subtraction counting as said measurement result;

and wherein said guiding unit is formed as a rod-like body having one end section thereof rotatably connected to said housing, the other end section of the rod-like body constitutes the distal end section where said latching section is provided, and the measuring belt that has been drawn out from said housing is guided till the distal end section is reached along said guiding unit, and said latching tool is latched with said latching section and cues the measuring belt.

13. The length measuring instrument according to claim 12, wherein said optical modulating section comprises a rotary optical modulation plate fixed to said rotary shaft, and said rotary optical modulation plate comprises a transparent disk and a plurality of portions for regulating the quantity of transmitted light arranged successively and adjacently on the surface of said transparent disk.

14. The length measuring instrument according to claim 13, wherein some of a plurality of said portions for regulating the quantity of transmitted light are light-shielding areas and the remaining part of a plurality of said portions for regulating the quantity of transmitted light are light-transmitting areas of different width in the rotation direction of said rotary optical modulation plate.

15. The length measuring instrument according to claim 13, wherein a plurality of said portions for regulating the quantity of transmitted light are light-transmitting areas with different light transmittances.

16. The length measuring instrument according to claim 12, wherein said optical modulating section is constituted as a rotary optical modulation plate provided directly or indirectly on the rotary shaft, and said rotary optical modulation plate comprises a transparent disk and a plurality of portions for regulating the quantity of transmitted light arranged successively and adjacently on the surface of said transparent disk.

17. The length measuring instrument according to claim 16, wherein some of a plurality of said portions for regulating the quantity of transmitted light are light-shielding areas and the remaining part of a plurality of said portions for regulating the quantity of transmitted light are light-transmitting areas of different width in the rotation direction of said rotary optical modulation plate.

18. The length measuring instrument according to claim 16, wherein a plurality of said portions for regulating the quantity of transmitted light are light-transmitting areas with different light transmittances.

* * * * *